United States Patent [19]

Taylor

[11] Patent Number: 5,001,225

[45] Date of Patent: Mar. 19, 1991

[54] MONOCLONAL ANTIBODIES TO A PAN-MALARIAL ANTIGEN

[75] Inventor: Diane W. Taylor, Potomac, Md.

[73] Assignee: Georgetown University, Washington, D.C.

[21] Appl. No.: 939,113

[22] Filed: Dec. 8, 1986

[51] Int. Cl.[5] .................... C07K 15/00; C12N 5/00
[52] U.S. Cl. .................... 530/387; 530/388; 530/808; 530/809; 435/70.21; 435/172.2; 435/240.26; 435/240.27; 424/85.8; 436/547; 436/548; 935/89; 935/95; 935/106; 935/107; 935/108
[58] Field of Search .............. 530/387, 808, 809, 388; 435/68, 172.2, 240.26, 240.27; 424/85, 85.8; 935/89, 95; 436/547-548

[56] References Cited

U.S. PATENT DOCUMENTS 4,837,016  6/1989  Holder et al.

FOREIGN PATENT DOCUMENTS 2114288  8/1983  United Kingdom.
2154592  9/1985  United Kingdom.

OTHER PUBLICATIONS

Lyon, *PNAS* 83, 1986, pp. 2989-2993.
Holder et al., *J. Exp. Med.* 1982, vol. 156, pp. 1528-1538.
Odink et al., *FEBS* 1984, vol. 173(1) pp. 108-112.
Parson et al., *J. Immunol.* 134, 1985, pp. 1946-1951.
Jendouhi et al., *J. Immunol.* 134, 1985, pp. 1941-1945.
Charoenvit, *Infection and Immunity*, 55: 604-608 (1987).
Taylor, *Infection and Immunity*, 51: 884-890 (1986).
Holder, *Chem. Abstract* 100: 211-219 (1984).
Wiser, *Eur. Journ. Cell Biolo.*, Biological Abst. No. 83065696, 42(1): 45-51 (1986).
Plorde, J. J., "Malaria," in R. G. Petersdorf et al., eds., *Harrison's Principles of Internal Medicine*, Tenth Edition, McGraw-Hill Co., Pub., N.Y., pp. 1187-1193 (1983).
Winchell, E. J., et al., *Molecular and Biochemical Parasitology* 10: 287-296 (1984).
Wilson, R. J. M., et al., *Lancet* ii: 201-205 (1969).
Anders, R. F. et al., *Proc. Natl. Acad. Sci. USA* 80: 6652-6656 (1983).
Cowman, A. F. et al., *Cell* 40: 775-783 (1985).
Wilson, R. J. M., *Nature* (London) 284: 451-452 (1980).
Coppell, R. L. et al., *Nature* (London) 306: 751-756 (1983).
Saul, A. et al., *Parasite Immunol.* 6: 39-50 (1984).
Saul, A. et al., *Parasite Immunol.* 7: 587-593 (1986).
McGregor, I. A., *Br. Med. Bull.* 28: 22-27 (1972).
Houba, V., *Bull W.H.O.* 52: 199-207 (1975).
Taylor, D. W. et al., *Exp. Parasitol* 53: 362-370 (1981).
Potocnyak, P. et al., *Science* 215: 1637 (1982).
Wahl, et al., *J. Nuclear Med.* 24(4): 316-325 (1983).
Langhorne, J. et al., *Cell Immunol.* 87: 452-461 (1984).
Holder, A. A. et al., *Nature* 294: 361-364 (1981).

*Primary Examiner*—Garnette D. Draper
*Attorney, Agent, or Firm*—Saidman, Sterne, Kessler & Goldstein

[57] ABSTRACT

A continuous hybridoma cell line, designated 7H8, which secretes a monoclonal antibody (MAb 7H8) of the IgM class and which binds to a protein present in species of the genus Plasmodium. MAb 7H8 also recognizes an antigen (antigen Pf93) unique to *P. falciparum*. Methods of isolating the substantially pure antigen using the antibody of the present invention are disclosed. MAb 7H8 is well suited for use in immunometric assays. Preferred is a two-sited assay developed with MAb 7H8. Anti-idiotypic and anti anti-idiotypic antibodies to MAb 7H8 are disclosed. The antibodies and antigens of the present invention are useful for immunodiagnostic and immunotherapeutic treatment of malarial diseases of man and animals.

4 Claims, 21 Drawing Sheets

FIG. 8

A PORTION OF Pf93 WAS PRODUCED IN A
LAMDA gtII/E. coli Y1090 SYSTEM.

RESULTS SHOWED THAT

--- REGION DOES NOT CONTAIN TAMDEM REPEATS
--- HAS NO SEQUENCE HOMOLOGY WITH THE S-Ag
--- DNA DOES NOT CROSS HYBRIDIZE WITH THE GENE FOR THE 195Kd MEROZOITE SURFACE PROTEIN

Two-Sided Assay

MONOCLONAL ANTIBODIES TO A PAN-MALARIAL ANTIGEN

BACKGROUND OF THE INVENTION

1. Field of the Invention

The present invention relates to a hybridoma cell line, designated 7H8, which secretes an IgM monoclonal antibody (MAb), designated MAb 7H8. MAb 7H8 binds to an antigen associated with organisms of the genus Plasmodium. The present invention is further directed to the discovery that MAb 7H8 is capable of binding to a novel antigen, designated Pf93, associated with *P. falciparum*. The present invention is further directed to anti-idiotypic antibodies and to anti anti-idiotypic antibodies directed against MAb 7H8. The present invention further relates to methods of detecting plasmodial infections in animals including humans employing MAb 7H8, to methods of suppressing plasmodial infections in animals, and to vaccines for and methods of vaccinating against *P. falciparum*.

2. Brief Description of the Background Art

Malaria, a protozoan disease transmitted to humans by the Anopheles mosquito, is a serious infectious disease endemic to many parts of the world, especially tropical and subtropical regions. The disease is characterized by fever, rigors, anemia, splenomegaly, and chronic relapsing course.

Malaria is caused by protozoan organisms of the genus *Plasmodium*. Humans are infected by at least four species: *P. vivax*, *P. ovale*, *P. malariae*, and *P. falciparum*. A female anopheline mosquito inoculates plasmodial sporozoites into the lymphohematogenous system while feeding. Following a brief stay in the peripheral blood system, the organisms invade hepatocytes, where they initiate the preclinical hepatic (exoerythrocytic) phase of the disease. A single sporozoite can produce 2,000 to 40,000 hepatic merozoites by a process of asexual multiplication known as schizogony. The daughter cells thus produced rupture back into the circulatory system in one to six weeks. This marks the end of the preclinical hepatic stage in some plasmodial species (*P. falciparum* and *P. malariae*), but other plasmodial species have persistent hepatic phases which produce episodes of bloodstream invasion for months and even years.

The clinical (erythrocytic) phase of malaria begins with the attachment of a released merozoite to the surface of a red blood cell. The merozoite attaches at a specific receptor site, which varies for each malarial species. After attachment, the merozoite slowly works its way into the interior of the red blood cell. Once inside, the parasite appears as a ring-shaped trophozoite. The trophozoite later enlarges and becomes ameboid in appearance. The nucleus of the trophozoite later divides into several portions forming a multinucleated schizont. Cell cytoplasm slowly condenses around each daughter nucleus forming a new generation of merozoites. The invaded erythrocyte ruptures 48 to 72 hours later, releasing this new generation of merozoites, each of which can initiate a new red blood cell cycle.

As the red blood cell invasion cycle is repeated, some red blood cells become filled with sexual forms of the parasite (gametocytes). Gametocytes do not induce cell lysis, and will not develop further unless ingested by an Anopheles mosquito during a blood meal. Fertilization occurs in the stomach of the mosquito, and the resulting ookinete later forms a cyst on the outer surface of the mosquito's stomach, releasing many sporozoites. These sporozoites migrate to the mosquito's salivary glands and are inoculated into a human at the next blood meal, thus completing the cycle.

The most common diagnostic test for malaria is examination of an appropriately stained blood film. Morphological differences among the plasmodial species infecting humans allow identification in blood smears. Usually, fingertip blood is smeared on a glass slide and stained with Wright's, Giemsa's, or Field stain. Thick smears have the advantage of concentrating parasites. However, numerous artifacts will be found in such smears, with the result that a great deal of experience is required to correctly interpret such preparations.

Thin smears are easier to examine and have fewer artifacts. At the same time, the relative paucity of cells in a thin smear increases the likelihood that a diagnosis will be missed. Additionally, because the intensity of parasitemia varies greatly from hour to hour, frequent repeated examinations of blood smears may be required (e.g., every eight hours for two-three days), which may be prohibitively labor-intensive, especially in endemic areas. The etiology, epidemiology, pathology, diagnosis, treatment, and prevention of malaria are described in Plorde, J.J., "Malaria", in, R.G. Petersdorf et al. eds. *Harrison's Principles of Internal Medicine*, Tenth Edition, McGraw-Hill Co., Publisher, New York, pp. 1187-1193 (1983).

It is known that antiplasmodial antibodies are produced during malarial infection in animals. For example, using hybridoma technology, Taylor, D.W., et al., *Infection Immunity* 32(2):563-570 (1981), identified monoclonal antibodies (MAbs) to *Plasmodium voelii*, a rodent malarial parasite. These MAbs identified stage-specific, species-specific, and cross-reactive antigens. The antigens were found on the surface or within the cytoplasm of the parasite, but not on the surface of erythrocytes from infected animals.

Malarial antigens are also known to appear in the serum of humans infected with *P. falciparum*. McGregor, I.A., et al., *Lancet* 1:881-884 (1968). The antigens may be secreted from infected erythrocytes or released during erythrocyte rupture and reinvasion. Winchell, E.J., et al., *Molecular Biochemistry and Parasitology* 10:287-296 (1984). Some circulating malarial antigens are biochemically stable to heating in boiling water for five minutes, and are thus termed heat-stable (S) antigens. Wilson, R.J.M., et al., *Lancet* 11:201-205 (1969). S antigens from various isolates of *P. falciparum* show substantial antigenicity. Anders, R.F., et al., *Proc. Natl. Acad. Sci. USA* 80:6652-6656 (1983); Cowman, A.F., et al., Cell 40:775 (1985); Wilson, R.J.M., *Nature* (London) 84:451-452 (1980). The immunologic importance of S antigens is unclear, but they have been implicated in both immune protection (Coppell, R.L., et al., *Nature* (London) 306:751-756 (1983); McGregor, I.A., et al., *Lancet* 1:881-884 (1968); Saul, A., et al., *Parasite Immunol.* 6:39-50 (1984); Saul, A., et al., *Parasite Immunol.*, in press) and immune suppression (McGregor, I.A., *Br. Med. Bull.* 28:22-27 (1972); Wilson, R.J.M., et al., Lancet 11:201-205 (1969)). In addition, circulating antigens may form immune complexes and may thus play an important role in the pathogenesis of malaria, especially glomerulonephritis. Houba, V., *Bull. W. H. O.* 52:199-207 (1975).

A need, therefore, has existed and continues to exist for a convenient method of general application for the serodiagnosis of malaria in animals, including humans.

Such a serodiagnostic method preferably would employ a monoclonal antibody specific for plasmodium-associated antigen. If an antibody were found that recognized an antigen common to all plasmodial species, this would allow the convenient identification of plasmodial infection, as, for example, in an initial screening.

SUMMARY OF THE INVENTION

Recognizing the need for a monoclonal antibody having the characteristics described above, the present inventor succeeded in isolating a hybridoma cell line, designated cell line 7H8, which secretes an IgM monoclonal antibody, designated MAb 7H8, which binds to a protein (antigen) present in organisms of the genus Plasmodium. MAb 7H8 thus identifies a pan-species malarial antigen, and is suitable for use in immunoassays. Moreover, the present inventor has developed a two-sited assay with MAb 7H8 which takes advantage of the discovery that the 7H8 antigen has at least two epitopes per molecule. It has also been discovered that MAb 7H8 recognizes a unique antigen (Pf93) found only in *P. falciparum*. MAb 7H8 thus may be used to isolate *P. falciparum* antigen Pf93, as well as for identification of general plasmodial infection. Anti-idiotypic and anti anti-idiotypic antibodies have also been developed according to the present invention. The antigens and antibodies of the present invention are useful in immunodiagnostic and immunotherapeutic methods for the detection and treatment of plasmodial infections in animals, including humans.

BRIEF DESCRIPTION OF THE DRAWINGS

FIG. 8. Indirect Immunofluorescence pattern produced by normal mouse serum (negative control), immune serum on rings, trophozoites and schizonts, and MAb 7H8 on *P. voelii* and *P. falciparum*.

DETAILED DESCRIPTION OF THE PREFERRED EMBODIMENTS

The present invention relates to a monoclonal antibody (MAb 7H8) which identifies a pan-malarial antigen (Ag-7H8). This MAb is produced by a continuous hybridoma cell line (cell line 7H8) generated by infecting BALB/c mice with $10^4$ 17XL *P. voelii* parasites. This monoclonal antibody is well suited for immunological detection of species of the *genus Plasmodium*, including *P. voelii, P. berghei, P. falciparum, P. vinckei, P. chabaudi, P. knowlesi, P. gallinaceum, P. vivax, P. ovale,* and *P. malariae*. MAb 7H8 is secreted by a continuous hybridoma cell line, deposited at the American Type Culture Collection, 12301 Parklawn Drive, Rockville, Maryland 20852, on Dec. 5, 1986, having accession number HB 9287. Thus, in one embodiment, the present invention provides for a continuous hybridoma cell line characterized in that it is capable of producing a monoclonal antibody having the specificity of the monoclonal antibody produced by hybridoma cell line 7H8. In another embodiment, the present invention provides for a continuous hybridoma cell line capable of secreting a monoclonal antibody reactive with an antigen (Ag-7H8), said antigen characterized in that:

(1) the major form of the antigen has a molecular weight of about 120,000, with minor components of 220,000, 65,000 to 75,000, and 45,000 in *P. veolii;*

(2) it remains antigenic after boiling for five minutes; and (3) said antigen can be bound by monoclonal antibody 7H8.

In yet another embodiment, the present invention provides for a monoclonal antibody having the specificity of MAb 7H8, said MAb 7H8 characterized in that it is produced by the hybridoma cell line 7H8.

The inventor has also discovered that MAb 7H8 identifies an antigen that is unique to one particular species of *Plasmodium*, namely *P. falciparum*. This antigen, designated Pf93, may be isolated in substantially pure form, employing MAb 7H8 of the present invention. Thus, an embodiment of the present invention provides for substantially pure antigen Pf93, said antigen characterized in that it is recognized by and binds to MAb 7H8. In another embodiment, the present invention provides for a monoclonal antibody capable of binding to the Pf93 antigen, said monoclonal antibody characterized in that it has the specificity of monoclonal antibody 7H8. In yet another embodiment, the present invention provides for a substantially purified *P. falciparum* antigen obtainable by:

(a) solubilizing *P. falciparum* cells containing said antigen;

(b) contacting the thus solubilized *P. falciparum* of step (a) with a monoclonal antibody having the specificity of MAb 7H8, thereby forming a complex of said antigen and said monoclonal antibody;

(c) substantially isolating said complex; and (d) separating said antigen from said monoclonal antibody.

The substantially pure antigen Pf.93 of the present invention may in turn be used to detect or measure antibody to plasmodial infection by *P. falciparum* in a sample, such as serum. Thus, one embodiment of the present invention comprises a method of detecting the presence or amount of antibody to plasmodium-associated antigen in a sample, comprising contacting said sample containing said antibody to plasmodium-associated antigen with detectably-labeled Pf93, and detecting said label. In addition to antigen Pf93 itself, one may also use immunoreactive fractions and immunoreactive analogues of Pf93. By the term "immunoreactive reactive fractions(s)" is intended a portion of the Pf93 antigen which demonstrates the equivalent immune response to the 7H8 antibody. By the term "immunoreactive analogue" is intended a protein which differs from the Pf93 protein by one or more amino acids but which demonstrates the equivalent immune response to antibody 7H8.

MAb 7H8 is well suited for use in standard immunodiagnostic assays well-known in the art, including such immunometric or "sandwich" assays as the forward sandwich, reverse sandwich, and simultaneous sandwich assays In this regard, the monoclonal antibody of the present invention may be used in combination with one or more other monoclonal antibodies specific for the Plasmodium genus or for particular Plasmodium species. The present inventor has discovered that the antigen 7H8 has at least two similar epitopes per molecule. As a result, a two-sited assay developed by the present inventor is a preferred form of immunoassay according to the present invention. Thus, in one embodiment, the present invention provides a method of determining the presence or amount of plasmodium-associated antigen in a sample, comprising:

(a) binding MAb 7H8 to an insoluble phase;

(b) adding a sample suspected of containing soluble plasmodium-associated antigen;

(c) adding detectably labeled MAb 7H8 to the soluble phase;

(d) removing unbound detectably labeled MAb 7H8; and (e) detecting said label.

In yet another embodiment, the present invention provides a method of determining the presence or amount of plasmodium-associated antigen in a sample comprising:

(a) binding partially purified MAb 7H8 to microtiter wells;

(b) adding either parasite extract or plasma samples containing soluble antigens;

(c) adding alkaline-phosphatase-labeled MAb 7H8; and (d) adding a substrate and recording the subsequent amount of color development.

Figure 1:
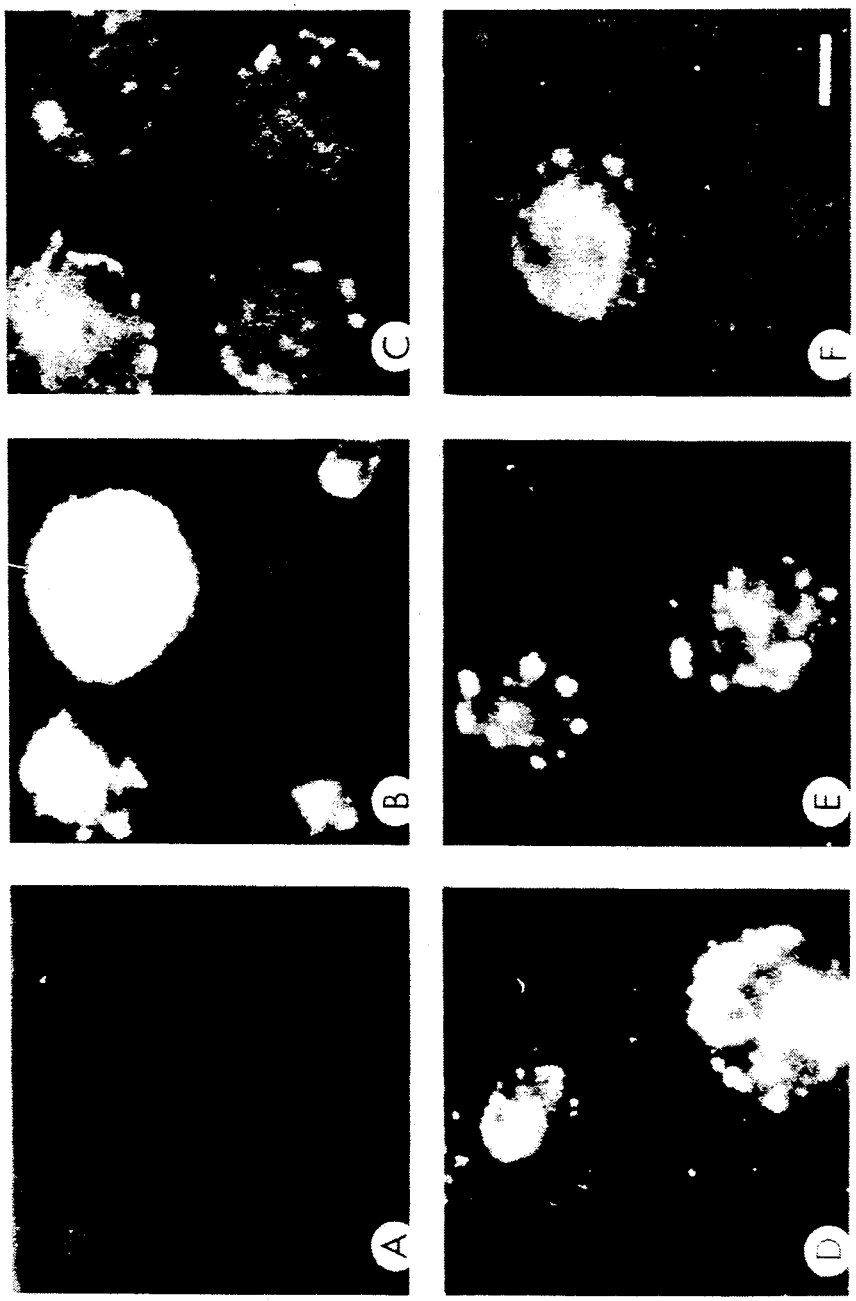
FIG. 1. IIF patterns. *P. voelii* (17XL) parasites were treated with (A) normal mouse serum, (B) polyspecific immune serum, and (C) MAb 7H8. MAb 7H8 produced a similar pattern of fluorescence when assayed on (D) 17XNL *P. voelii*, (E) *P. berghei*, and (F) P. falciparum. Bar, 3 um.

Although the inventor's present data suggest that there may be no therapeutic utility, the antibody and substantially purified antigens of the present invention also may be useful for the therapeutic treatment of plasmodial infections. Thus, one embodiment of the present invention provides a method of suppressing a plasmodial infection in an animal which comprises administering to said animal a therapeutically effective amount of a monoclonal antibody having the specificity of MAb 7H8. In yet another embodiment, the present invention provides a pharmaceutical composition comprising plasmodial infection-suppressing amounts of MAb 7H8, together with a pharmaceutically inert carrier.

Those of skill will appreciate that preventing plasmodial infection is greatly to be preferred where possible. Using the monoclonal antibody of the present invention, it may be possible to immunize an animal, such as a human, against plasmodial infection. Thus, one embodiment of the present invention provides a method of immunizing an animal against plasmodial infection which comprises administering to said animal an effective amount of a monoclonal antibody having the specificity of MAb 7H8. It will also be appreciated that anti-idiotypic and anti anti-idiotypic antibodies to MAb 7H8 may be generated, which will be useful for vaccines, passive immunization, and the like. Thus, another embodiment of the present invention comprises an anti-idiotypic antibody to MAb 7H8. Yet another embodiment of the present invention comprises an anti anti-idiotypic antibody to MAb 7H8. A further embodiment of the present invention comprises a method of actively immunizing an animal against plasmodial infection comprising administering to said animal effective amounts of an anti-idiotypic antibody to MAb 7H8 or passively immunizing an animal by administering effective amounts of an anti anti-idiotypic antibody to MAb 7H8.

In the following description, reference will be made to various methodologies well known to those skilled in the art of immunology. Applications and other materials setting forth such well-known methodologies will be referred to in the course of this description, and are incorporated herein by reference in their entirety as set forth herein in full. Standard reference works setting forth the general principles of immunology include Klein, J. *Immunology: The Science of Self-Nonself Discrimination*, John Wiley & Sons, Publisher, New York (1982); Kennett, R., et al., eds., *Monoclonal Antibodies, Hybridoma: A New Dimension in Biological Analyses*, Plenum Press, Publisher, New York (1980); Campbell, A., "Monoclonal Antibody Technology", in, Burdon, R., et al., eds., *Laboratory Techniques in Biochemistry and Molecular Biology*, Volume 13, Elsevier, Publisher, Amsterdam (1984).

By "detecting" it is intended to include determining the presence or absence of a substance or quantifying the amount of a substance. The term thus refers to the use of the materials, compositions, and methods of the present invention for qualitative and quantitative determinations.

By "plasmodial infection" is meant any infection of an animal, including a human, caused by any species of the genus *Plasmodium*. A preferred species for the purposes of the present invention is *P. falciparum*.

By "plasmodium-associated antigen" is meant any antigen associated with a species of the genus *Plasmodium*, which antigen is expressed during the course of infection in its animal host. Such antigens may be associated with the surface of the parasite, or may be released by the parasite into the host RBC and then into serum. The latter are preferred for the purposes of the present invention. Particularly preferred is the so-called 7H8 family of conserved antigens. These antigens are expressed by many different *Plasmodium* species, and are recognized by MAb 7H8. They are thus referred to as the "pan-malarial" antigens. Even more preferred is the Pf93 antigen, which is unique to *P. falciparum*.

The procedures for the production of the monoclonal antibody of the present invention are described in Taylor, D.W., et al., *Infection Immun.* 32(a):563–570 (1981), incorporated herein by reference. Briefly, BALB/c mice were infected with 17XL *P. voelii* parasites. Mice were killed when parasitemias reached about 54%, and a suspension of spleen cells was prepared and fused with the P3-X63-NS/1 cell line. Hybrids were selected in a hypoxanthine-aminopterinethymidine medium and screened by indirect immunofluorescence (IIF) with acetone-fixed smears of *P. voelii* and by radioimmunoassay as described by Taylor, D.W., et al., *Exp. Parasitol.* 53:362–370 (1981), with extracts of 17XL and 17XNL parasites. The hybrid cell line (7H8) used in this study was cloned twice by limiting dilution. Ascites was produced in pristane-primed mice. The isotype of the hybrid was determined by polyethylene glycol Ouchterlony analysis, immunoelectrophoresis, and an isotype-specific radioimmunoassay as described by Taylor, D.W., et al., *Exp. Parasitol.* 53:362–370 (1981).

The isolation of other hybridomas secreting monoclonal antibodies of the same specificity as those described herein can be accomplished by the technique of anti-idiotypic screening. Potocnjak, et al., *Science* 215:1637 (1982). Briefly, an anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody). By using the anti-idiotypic antibody of the second animal, which is specific for the monoclonal antibodies produced by a single clone, it is then possible to identify other clones used for immunization. Idiotypic identity between the product of two clones demonstrates that the two clones are identical with respect to their recognition of the same epitopic determinants. The anti-idiotypic antibody may also be used as an "immunogen" to induce an immune response in yet another animal, producing a so-called anti anti-idiotypic antibody which will be epitopically identical to the original MAb. Thus, by using antibodies to the epitopic determinants of a monoclonal antibody, it is possible to identify other clones expressing antibodies of identical epitopic specificity. In antibodies, idiotypic determinants are present in the hypervariable region which binds to a given epitope Accordingly, the monoclonal antibody of the present invention may be used to induce anti-idiotypic Abs in BALB/c mice. Spleen cells from these animals are used to produce anti-idiotypic hybridoma cell lines. Monoclonal anti-idiotypic Abs coupled to KLH are used as "immunogen" to immunize BALB/c mice. Sera from these mice will contain anti anti-idiotypic Abs that have the binding properties of the original Ab specific for the shared epitope. The anti-idiotypic MAbs thus have idiotopes structurally similar to the epitope being evaluated.

For replication, the hybrid cells may be cultivated both in vitro and in vivo. High in vivo production makes this the presently preferred method of culture. Briefly, cells from the individual hybrid strains are injected intraperitoneally into pristane-primed BALB/C mice to produce ascites fluid containing high concentrations of the desired monoclonal antibodies. Monoclonal antibodies of isotype IgM may be purified from cultured supernatants using column chromatography methods well known to those of skill in the art.

The monoclonal antibody of the present invention is particularly suited for use in immunoassays wherein it may be utilized in liquid phase or bound to a solid phase carrier. In addition, the monoclonal antibody in these immunoassays can be detectably labeled in various ways.

The term "antibody" (Ab) as used in this invention is meant to include intact molecules as well as fragments thereof, such as, for example, Fab and F(ab')$_2$' which are capable of binding antigen. Fab and F(ab')$_2$ fragments lack the Fc fragment of antibody, clear more rapidly from the circulation, and may have less nonspecific tissue binding than intact antibody. Wahl et al., *J. Nuclear Med.* 24(4):316–325 (1983). It will be appreciated that Fab, F(ab')$_2$ and other fragments of the monoclonal antibody of the present invention may be used as well as the intact antibody for the detection and treatment of plasmodial antigens according to the methods of the present invention.

There are many different labels and methods of labeling known of those of ordinary skill in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to the monoclonal antibody, or will be able to ascertain the same by the use of routine experimentation. Furthermore, the binding of these labels to the monoclonal antibody can be accomplished using standard techniques commonly known to those of ordinary skill in the art.

One of the ways in which a monoclonal antibody of the present invention can be detectably labeled is by linking the monoclonal antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the monoclonal antibodies of the present invention include malate dehydrogenase, staphyloccocal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled monoclonal antibody of the present invention can also be detected by labeling the monoclonal antibody with a radioactive isotope which can then be determined by such means as the use of a gamma counter or a scintillation counter. Isotopes which are particularly useful for the purpose of the present invention are $^3H$, $^{125}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to detect the binding of the detectably labeled monoclonal antibody of the present invention by labeling the monoclonal antibody with a fluorescent compound. When the fluorescently labeled monoclonal antibody is exposed to light of the proper wave length, its presence can then be detected due to the fluorescence of the dye. Among the most commonly used fluorescent labelling compounds are fluoroscein isothiocyanate, rhodamine, phycoerytherin, phycocyanin, allophycocyanin, o-phthaldehyde and fluorescamine.

The monoclonal antibody of the invention also can be detectably labeled using fluorescent emitting metals such as $^{152}Eu$, or others of the lanthanide series. These metals can be attached to the antibody molecule using such metal chelating groups as diethylenetriaminepentaacetic acid (DTPA) or ethylenediaminetetraacetate acid (EDTA).

The monoclonal antibody of the present invention also can be detectably labeled by coupling it to a chemiluminescent compound. The presence of the chemiluminescent-tagged monoclonal antibody is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the monoclonal antibody of the present invention. Bioluminescence is a type of chemiluminescence found in biological systems in which a catalytic protein increases the efficiency of the chemiluminescent reaction. The presence of a bioluminescent monoclonal antibody is determined by detecting the presence of luminescence. Important bioluminescent compounds for purposes of labeling are luciferin, luciferase and aequorin.

For the purposes of the present invention, plasmodial-associated antigen which is detected by the monoclonal antibody of the invention may be present in biological fluids and tissues. Any sample containing the detectable yet unknown amount of plasmodial-associated antigen can be used. Normally, the sample is a liquid, such as, for example, urine, saliva, cerebrospinal fluid, blood, serum and the like, or a solid or semi-solid, such as, for example, tissue, feces and the like.

Another technique which may also result in greater sensitivity when used in conjunction with the present invention consists of coupling the monoclonal antibody of the present invention to low molecular weight haptens. The haptens can then be specifically detected by means of a second reaction. For example, it is common to use such haptens as biotin (reacting with avidin) or dinitrophenyl, pyridoxal and fluorescamine (reacting with specific antihapten antibodies) in this manner.

The term "epitope" as used in this invention is meant to include any determinant responsible for specific interaction with an antibody molecule. Epitopic determinants usually consist of chemically active surface groupings of molecules such as amino acids or sugar side chains and have specific three-dimensional structural characteristics, as well as specific charge characteristics.

For in vivo diagnosis, radionucleotides may be bound to the monoclonal antibodies of the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}$Tc, $^{123}$I, $^{111}$IN, $^{131}$I, $^{97}$Ru, $^{67}$Cu, $^{67}$Ga and $^{68}$Ga The monoclonal antibodies of the invention can also be labeled with non-radioactive isotopes for purposes of in vivo diagnosis. Elements which are particularly useful in this manner are $^{157}$Gd, $^{55}$Mn, $^{162}$ $^{52}$Cr and $^{56}$Fe.

The monoclonal antibody of the present invention also may be used for immunotherapy in animals, including humans, having a malarial infection which expresses plasmodial-associated antigen with epitopes reactive with the monoclonal antibody of the present invention. When used for immunotherapy, the monoclonal antibody of the present invention may be unlabeled or labeled with a therapeutic agent. Examples of therapeutic agents which can be coupled to the monoclonal antibodies of the invention for immunotherapy are drugs, radioisotopes, lectins and toxins.

Lectins are proteins, usually isolated from plant material, which bind to specific sugar moieties. Many lectins are also able to agglutinate cells and stimulate lymphocytes. Ricin is a toxic lectin which has been used immunotherapeutically. This use is accomplished by binding the alpha-peptide chain of ricin, which is responsible for toxicity, to the antibody molecule to enable site-specific delivery of the toxic defect.

Toxins are poisonous substances produced by plants, animals or microorganisms that, in sufficient dose, are often lethal. Diphtheria toxin, for example, is a protein produced by *Corynebacterium diphtheria*. This toxin consists of an alpha and a beta subunit which under proper conditions can be separated. The toxic alpha component can be bound to antibody and used for a site-specific delivery.

Examples of radioisotopes which can be bound to the monoclonal antibodies of the present invention for use in immunotherapy are: $^{125}$Um, $^{131}$I, $^{90}$Y, $^{67}$Cu, $^{217}$Bi, $^{211}$At, $^{212}$Pb, $^{47}$Sc and $^{109}$Pd.

It is also possible to utilize liposomes having the monoclonal antibody of the present invention in their membrane to specifically deliver the liposomes to the target area. These liposomes can be produced so that they contain, in addition to the monoclonal antibody, such immunotherapy agents as drugs, radioisotopes, lectins and toxins, which would be released at the target site.

The dose ranges for the administration of the monoclonal antibody of the present invention are those large enough to produce the desired effect, whereby the malarial symptoms are ameliorated. The doses should not be so large as to cause adverse side effects, such as unwanted cross reactions, anaphylactic reactions, and the like. Generally, the dosage will vary with the age, condition, sex and extent of the disease in the patient. Counterindications, if any, immune tolerance and other variables will also affect the proper dosage. The monoclonal antibody can be administered parenterally by injection or by gradual profusion over time. The monoclonal antibody of the present invention also can be administered intravenously, intraparenterally, intramuscularly or subcutaneously.

Preparations for parenteral administration include sterile or aqueous or non-aqueous solutions, suspensions and emulsions. Examples of non-aqueous solvents are propylene glycol, polyethylene glycol, vegetable oils such as olive oil, and injectable organic esters such as ethyloleate Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, inert gases and the like. See, generally, *Reminqton's Pharmaceutical Science*, 16th ed., Mac Eds. (1980).

The present invention also relates to a method of preparing a medicament or a pharmaceutical composition comprising the components of the invention, the medicament being used for therapy of animal, including human, malaria-expressing, or fractions or analogues thereof, antigen reactive with the monoclonal antibody of the present invention.

The monoclonal antibody and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the immunoassay to be used.

The types of immunoassays which can be incorporated in kit form are many. Typical examples of some of the immunoassays which can utilize the antibodies of the invention are radioimmunoassays (RIA) and immunometric, or sandwich, immunoassays.

By the term "immunometric assay" or "sandwich immunoassay", it is meant to include simultaneous sandwich, forward sandwich and reverse sandwich immunoassays. These terms are well understood by those skilled in the art. Those of skill will also appreciate that the monoclonal antibody of the present invention will be useful in other variations and forms of immunoassays which are presently known or which may be developed in the future. These are intended to be included within the scope of the present invention In a forward sandwich immunoassay, a sample is first incubated with a solid phase immunoabsorbent containing monoclonal antibody(ies) against the antigen Incubation is continued for a period of time sufficient to allow the antigen in the sample to bind to the immobilized antibody in the solid phase. After the first incubation, the solid phase immunoabsorbent is separated from the incubation mixture and washed to remove excess antigen and other interfering substances, such as non-specific binding proteins, which also may be present in the sample. Solid phase immunoabsorbent containing antigen bound to the immobilized antibody is subsequently incubated for a second time with soluble labeled antibody or antibodies. After the second incubation, another wash is performed to remove unbound labeled antibody(ies) from the solid phase immunoabsorbent and removing non-specifically bound labeled antibody(ies). Labeled antibody(ies) bound to the solid phase immunoabsorbent is then detected and the amount of labeled antibody detected serves as a direct measure of the amount of antigen present in the original sample. Alternatively, labeled antibody which is not associated with the immunoabsorbent complex can also be detected, in which case the measure is in inverse proportion to the amount of antigen present in the sample. Forward sandwich assays are described, for example, in U.S. Pat. Nos. 3,867,517; 4,012,294 and 4,376,110.

In carrying out forward immunometric assays, the process comprises, in more detail:
(a) first forming a mixture of the sample with the solid phase bound antibody(ies) and incubating the mixture for a time and under conditions sufficient to allow antigen in the sample to bind to the solid phase bound antibody(ies).
(b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoabsorbent;
(c) separating the solid phase immunoabsorbent from the mixture after the incubation in step (b); and
(d) detecting either the labeled antibody or antibodies bound to the antigen-antibody complex on the solid phase immunoabsorbent or detecting the antibody not associated therewith.

In a reverse sandwich assay, the sample is initially incubated with labeled antibody(ies), after which the solid phase immunoabsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110.

In carrying out reverse immunometric assays, the process comprises, in more detail;
(a) first forming a mixture of the sample with the soluble detectably labeled antibody for a time and under conditions sufficient to allow antigen in the sample to bind to the labeled antibody;
(b) adding to the mixture after the incubation of step (a) the solid phase bound antibodies and incubating the new resulting mixture for a time and under conditions sufficient to allow antigen bound to the labeled antibody to bind to the solid phase anti bodies;
(c) separating the solid phase immunoabsorbent from the incubating mixture after the incubation in step (b); and
(d) detecting either the labeled antibody bound to the solid phase immunoabsorbent or detecting the labeled antibody not associated therewith.

In a simultaneous sandwich assay, the sample, the immunoabsorbent having multiple immobilized antibodies thereon and labeled soluble antibody or antibodies are incubated simultaneously in one incubation step. The simultaneous assay requires only a single incubation and has a lack of washing steps. The use of a simultaneous assay is by far the preferred one. This type of assay brings about ease of handling, homogeneity reproducibility, linearity of the assays and high precision. The sample containing antigen, solid phase immunoabsorbent with immobilized antibodies and labeled soluble antibody or antibodies is incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labeled antibody to the solid phase, thereby increasing the signal. Typical conditions of time and temperature are two hours at 45° C., or twelve hours at 37° C.

Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for labeled antibody. For example, labeled antibody might be employed at a concentration of about 1-50 ng per assay, whereas immobilized antibody might have a concentration of 10-500 ng per assay per antibody. The labeled antibody might have a specific activity with, for instance, one radioiodine per molecule, or as high as two or more radioiodines per molecule of antibody.

Of course, the specific concentrations of labeled and immobilized antibodies, the temperature and time of incubation as well as other assay conditions can be varied, depending on various factors including the concentration of antigen in the sample, the nature of the sample and the like. Those skilled in the art will be able to determine operative and optimal assay conditions for each determination by employing routine experimentation.

After the single incubation period, the solid phase immunoabsorbent is removed from the incubation mixture. This can be accomplished by any of the known separation techniques, such as sedimentation and centrifugation. A washing step is not required prior to detection of bound labeled antibody. Detection can be performed by a scintillation counter, for example, if the label is a radioactive gamma-emitter, or by a fluorometer, for example, if the label is a fluorescent material. In the case of an enzyme label, the detection can be done by colorimetric methods employing a substrate for the enzyme.

In carrying out the simultaneous immunometric assay on a sample containing a multivalent antigen, the process comprises, in more detail:
(a) simultaneously forming a mixture comprising the sample, together with the solid phase bound antibody and the soluble labeled antibody or antibodies;
(b) incubating the mixture formed in step (a) for a time and under conditions sufficient to allow antigen in the sample to bind to both immobilized and labeled antibodies;
(c) separating the solid phase immunoabsorbent from the incubation mixture after the incubation; and
(d) detecting either labeled antibody bound to the solid phase immunoabsorbent or detecting labeled antibody not associated therewith.

Other such steps as washing, stirring, shaking filtering and the like may of course be added to the assays, as is the custom or necessity for any particular situation.

In the preferred mode for preforming the assays it is important that certain "blockers" be present in the incubation medium (usually added with the labeled soluble antibody). The "blockers" are added to assure that nonspecific proteins, protease, or human antibodies to mouse immunoglobulins present in the experimental sample do not cross-link or destroy the monoclonal antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e., nonspecific) monoclonal antibodies of the same class or subclass (isotype) as those used in the assays (e.g. $IgG_1$, $IgG_{2a}$, IgM, etc.) can be used as "blockers". The concentration of the "blockers" (normally 1–100,ug/ul) is important, in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 microgs/ml) to the buffer which contains the "blockers".

There are many solid phase immunoabsorbents which have been employed and which can be used in the present invention. Well known immunoabsorbents include glass, polystyrene, polypropylene, dextran, nylon and other materials; tubes, beads, and microtiter plates formed from or coated with such materials, and the like. The immobilized antibodies can be either covalently or physically bound to the solid phase immunoabsorbent, by techniques such as covalent bonding via an amide or ester linkage, or by absorption. Those skilled in the art will know many other suitable solid phase immunoabsorbents and methods for immobilizing antibodies thereon, or will be able to ascertain such, using no more than routine experimentation.

The materials and methods used in carrying out the present invention may be more fully understood by reference to the following examples, which examples are not intended in any manner to limit the scope of the present invention.

One aspect of the present invention involves the development of pan-malarial vaccines. There are various methods for preparing vaccines against viruses and bacteria. The basic preferred requirements for any vaccine and for a method for the preparation of a vaccine are that (1) the resulting vaccine contain the necessary antigenic determinants to induce formation of antibodies in the host; (2) the vaccine possess high immunogenic potential; (3) the resulting vaccine be safe enough to be administered without any danger of clinical infection, either for the recipient or any contact of the recipient, and therefore, the risk associated with vaccination be minimized, if not totally eliminated; (4) the resulting vaccine be devoid of any toxic side-effects, for example, fever from endotoxin present in killed or extracted cells; (5) the resulting vaccine be suitable for administration by an effective route, for example, oral, intranasal, topical or parenteral; (6) the resulting vaccine mimic closely the circumstances of natural infection; (7) the resulting vaccine be stable under conditions of long-term storage, and that said long-term storage be at room temperature; and (8) the resulting vaccine be compatible with the usual inert vaccine carriers. Those conditions can be achieved by the vaccines of the present invention.

In one embodiment of the present invention, vaccines prepared from PfΣantigen, its immunogenic fraction or analogue, or anti-idiotypic antibody to 7H8 antibody, comprise the antigenic component of the vaccine. It may be necessary or preferable to covalently link the antigenic component to an immunogenic carrier, i.e., bovine serum albumin or keyhole limpet hemocyanin. The vaccines of the present invention may be administered to any mammal susceptible to plasmodial infection. Human and non-human mammals may benefit as hosts.

Administration may be by parenteral, oral, intranasal, intravenous, intramuscular, subcutaneous, or any other suitable means. The dosage administered may be dependent upon the age, health, weight, kind of concurrent treatment, if any, and nature of the plasmodial organism. The vaccine may be employed in dosage forms such as capsules, liquid solutions, suspensions, or elixirs, for oral administration, or sterile liquid formulations such as solutions or suspensions. An inert, immunologically acceptable carrier is preferably used, such as saline or phosphate-buffered saline.

EXAMPLE I

MATERIALS AND METHODS

Strains of Mice and Parasites

In the majority of the studies, 6- to 8-week-old BALB/c mice (Cumberland View Farms, Clinton, Tenn.) were injected intraperitoneally (i.p.) with specified numbers of either the 7XL (lethal) or 17XNL (nonlethal) strain of *P. voelii*. Parasitemias were monitored every other day from Giemsa-stained tail blood smears. In studies comparing the kinetics of parasitemia and antigenemia, mice of the following strains were injected i.p. with 106 17XNL *P. voelii* parasites: AKR/J (Jackson Laboratory, Bar Harbor, Me.), C57BL/6Boy and C57BL/6(H-$2^k$) (NIAID breeding contact; Bioqual Inc., Rockville, MD). Parasites used in indirect immunofluorescence (IIF) studies included *Plasmodium berghei* (NYU/2) and *P. falciparum* (Malayan Camp strain) from Aotus monkeys.

Production of MAbs

Details of the procedures for the production of anti-*P. voelii* MAbs are described in, Taylor, D.W. et al., *Infect. Immun.* 32:563–570 (1981), incorporated herein by reference. Briefly, the hybridoma of the present invention was produced by infecting BALB/c mice with $10^4$ 17XL *P. voelli* parasites. When the parasitemias reached 54% 9 days later, the mice were killed, and a suspension of spleen cells was prepared and fused with the P3-X63-NS/1 cell line. Hybrids were selected in a hypoxanthine-aminopterin-thymidine medium and screened by IIF with acetone-fixed smears of *P. voelli*, Voller, A., *Bull. W.H.O.* 30:343–354, and by radioimmunoassay as described in, Taylor, D.W. et al., *Exp. Parasitol* 53:362–370 (hereinafter Taylor (I)), with extracts of 17XL and 17XNL parasites. The hybrid cell line (7H8) of the present invention was cloned twice by limiting dilution. Ascites was produced in pristane-primed mice. The isotype of the hybrid was determined by polyethylene glycol Ouchterlony analysis, immunoelectrophoresis, and an isotype-specific radioimmunoassay as previously described. Taylor,(I).

Molecular Weight of Ag-7H8

*P. voelii* parasites of the 17XL strain were cultured in vitro for 14 h in Selectamine (GIBCO Laboratories, Grand Island, N.Y.) in the presence of 1 uCi of [$^{35}$S] methionine as described in Langhorne, J., et al., *Cell. Immunol.* 89:452–461. Cells were harvested, washed three times with saline, and solubilized with 0.5% Nonidet P-40 in NET buffer (0.15 M NaCl, 2 mM EDTA, 0.5 M Tris: pH 7.4). Aliquots of labeled parasite proteins were adsorbed with protein A-Sepharose (Pharmacia Fine Chemicals, Piscataway, N.J.) and then incubated for 30 min with 5 ul of (i) normal mouse serum; (ii) immune mouse serum; (iii) ascites from the MAb 8B11 known to react with a protein of 230,000 $M_r$ in *P. voelli;* and (iv) MAb 7H8. Next, 50 ul of a 1:20 dilution of rabbit anti-mouse mu serum was added and incubated for 30 min at room temperature. Finally, 50 ul of a 50% slurry of protein A-Sepharose in NET buffer was added and the mixture was incubated for 45 min. Antigen-antibody-protein-A-Sepharose complexes were washed extensively, solubilized in sodium dodecyl sulfate (SDS)-sample buffer (nonreducing), and electrophoresed on a 10% slab SDS-polyacryl-amine gel (SDS-PAG) by the method of Laemmli. Laemmli, U.K., *Nature* 227:680–682 by the method of Laemmli. (1970). Gels were treated with En$^3$Hance (New England Nuclear Corp., Boston, Mass.), dried, and processed for autoradiography with X-Omat R film (Eastman Kodak Co., Rochester, N.Y.).

Molecular weight determinations were also made by Western blot analysis as described in Howard, R.J., *J. Cell Biol.* (in press). Extracts of 17XL *P. voelli*, prepared by freeze-thawing Percoll-enriched, *P. voelli*-infected erythrocytes, were incubated for 10 min at 37° C. in 5% SDS-5% 2-mercaptoethanol and then electrophoresed on a 5 to 15% SDS-PAG according to Laemmli. Laemmli, U.K., *Nature* 227:680–682 (1970). Proteins were transblotted onto nitrocellulose paper, Towbin, H., et al., *Proc. Natl. Acad. Sci. USA* 76:43–50–4354 (1979), overnight in a Hoefer apparatus (Hoefer Scientific Instruments, San Francisco, Calif.) at 30 V with Tris-glycine buffer plus 20% methanol. Nitrocellulose strips were then incubated successively with 2 ml of 0.3% Tween 20 plus 0.3% bovine serum albumin (BSA) in NET buffer, a 1:100 dilution of MAbs, a 1:1,000 dilution of rabbit anti-mouse immunoglobulin M (IgM), and $^{125}$I-protein A ( 30,000 cpm/ml; ICN Pharmaceuticals, Inc., Irvine, Calif.). Strips were dried on gel bond and autoradiographed as described above. High- and low-molecular weight standards (Bio-Rad Laboratories, Richmond, Calif.), were used throughout.

Antigen-Detection Assay

A two-sited assay was developed for detecting Ag-7H8 in the sera of infected mice. This assay consists of four major steps: (i) binding of partially purified MAb 7H8 to microtiter wells, (ii) adding either parasite extract or plasma samples containing soluble antigens, (iii) adding alkaline-phosphatase-labeled MAb 7H8, and finally (iv) adding a substrate and recording the subsequent amount of color development. Initially, MAb 7H8 was partially purified by a 50% ammonium sulfate precipitation. Then, 1 mg was coupled to 1,000 U of alkaline phosphate (Sigma Chemical Co., St. Louis, Mo.) by incubation with 0.25% glutaraldehyde for 2 h at room temperature, followed by extensive dialysis against phosphate-buffered saline (PBS), pH 7.4. In the two-sited assay, 100 ul of partially purified MAb 7H8 in PBS, at 100 ug/ml unless otherwise specified, was applied to the wells of flat-bottom polystyrene microtiter plates (Immunolon I; Dynatech Industries, Inc., McLean, Va.), and control wells were treated with 3% BSA (radioimmunoassay grade) in PBS. Plates were incubated overnight at 4° C. Wells were washed, treated with 200 ul of 3% BSA in PBS for 2 h at 37° C., and washed five times with PBS. Then, 50 ul of *P. voelii* extract, plasma samples diluted in 3% BSA in PBS, or PBS (used as a negative control for blanking the microplate reader) was added to triplicate wells and incubated overnight. After being washed five times with PBS, 100 ul of alkaline-phosphate-labeled 7H8 MAb (at a 1:500 dilution unless otherwise stated) was added. Plates were incubated for 2 h at 37° C. and washed three times with PBS, and 200 ul of 1 mg of p-nitrophenol substrate (Sigma P104) per ml of diethanolamine buffer was added. Color development was determined in about 30 min at 405 nm with an EL310 microplate reader (Bio-Tek Instruments, Inc., Burlington, Vt.).

The assay was initially developed with extracts of *P. voelii* parasites. During preparation of the extracts, blood samples from BALB/c mice with high 17XL *P. voelii* parasitemias were fractionated on a Percoll gradient to enrich for parasitized erythrocytes. Parasitized cells were freeze-thawed three times and centrifuged at 10,000×g for 30 min. The supernatant, designated as a water-soluble cell cytosol, was removed, and the remaining pellet was washed twice with saline and extracted with 1% Triton X-100. The supernatant, containing proteins released from the erythrocyte and parasite membranes, and the Triton-X-100-insoluble pellet, containing erythrocyte and parasite cytoskeletons, were saved. The protein concentrations of the three extracts were determined by a protein determining reagent (Bio-Rad).

In assays using boiled extracts or plasma, samples were placed in a rapidly boiling water bath for 5 min. The aggregated proteins were centrifuged at 1,000 x g for 10 min, and the clear, colorless supernatant was carefully removed and assayed immediately.

RESULTS

Description of MAb 7H8

MAb 7H8 has an IgM isotype. The antibody produced a characteristic pattern in an IIF assay, using acetone-fixed smears of infected erythrocytes (FIG. 1). Erythrocytes containing ring stage parasites were negative. However, a characteristic set of fluorescent spots can be seen in trophozoite- and schizont-containing erythrocytes (FIG. 1C through F). The fluorescent spots appear to be external to the parasitophorous vacuole membrane but internal to the erythrocyte membrane. Occasionally, the erythrocyte membrane ruptured during preparation of the smear, and discrete spots of fluorescence could be seen as released intact granules. Similar patterns of fluorescence were produced in erythrocytes infected with *P. berghei* and *P. falciparum* (FIG. 1E and F, respectively). In addition to fluorescence spots that appeared outside the parasite, there was strong fluorescence from the 17XNL *P. voelii* and *P. falciparum* parasites (trophosoites and schizonts) themselves (FIG. 1D and F). In contrast, 17LX *P. voelii* and *P. berghei* parasites were negative with intact erythrocytes and mechanically released intact, parasites demonstrated that the antigen is not expressed on these membrane surfaces.

Biochemical Studies

Figure 2:
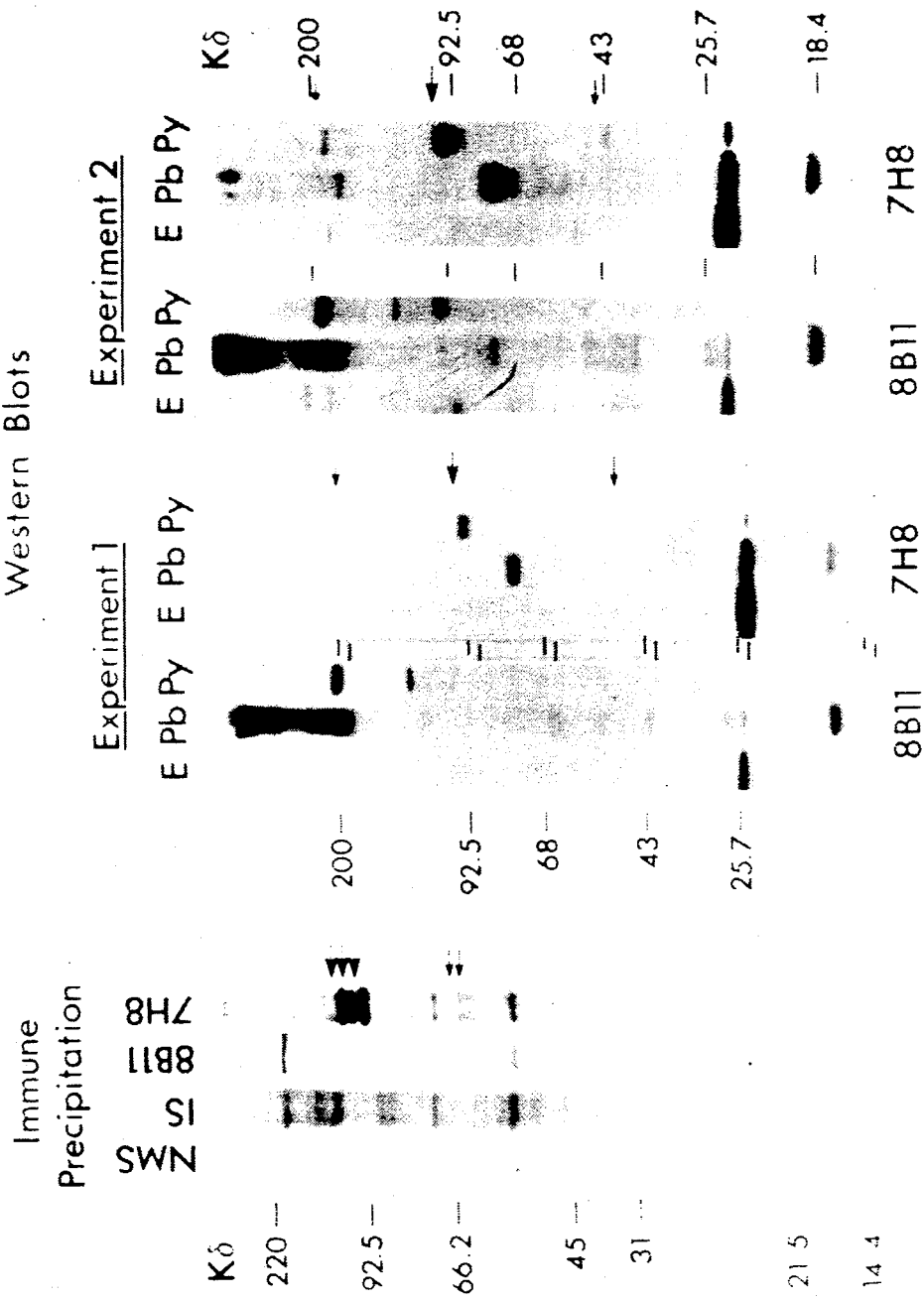
FIG. 2. Molecular weight determinations for antigens bound by MAb 7H8. Immune precipitation results were obtained when an extract of [$^{35}$S]methionine-labeled 17XL *P. voelii* parasites was immune-precipitated with normal mouse serum (NMS) (lane 1), immune serum (IS) (lane 2), MAb 8B11 to a *P. voelii* antigen of 230 kDa (lane 3), and MAb 7H8 (lane 4). Immune precipitates were assayed on a 10% SDS-PAGE under nonreducing conditions. Western blot analysis: extracts of either normal mouse erythrocytes (E), *P. berghei* (Pb)-, or *P. voelii* (Py)-infected erythrocytes were separated on a 5 to 15% SDS-PAGE under reducing conditions and then electrophoresed onto nitrocellulose paper. Samples were treated with 8B11, an IgM MAb to a 230,000-kDa protein of *P. voelii* known to cross-react with *P. berghei* and MAb 7H8.

Immune precipitation studies with [$^{35}$S]methionine-labeled parasites were conducted to determine the molecular weight of the antigen bound by MAb 7H8 (FIG. 2). Under nonreducing conditions, the antigen appeared as a doublet or triplet at 120, 135, and 148 kilodaltons (kDa) (large arrows), with several lesser bands between 65,000 and 75,000 (small arrows). Similar results were obtained by Western blot analysis under reducing conditions (FIG. 2). A predominant protein band of 117,000 to 120,000 (large arrows) was present with lesser bands at molecular weights of 200,000 and 45,000 (small arrows). MAb 7H8 also identified a protein in *P. berghei* with the significantly lower molecular weight of approximately 90,000.

Development of a Two-Sited Assay for Detecting Ag-7H8

Figure 3:
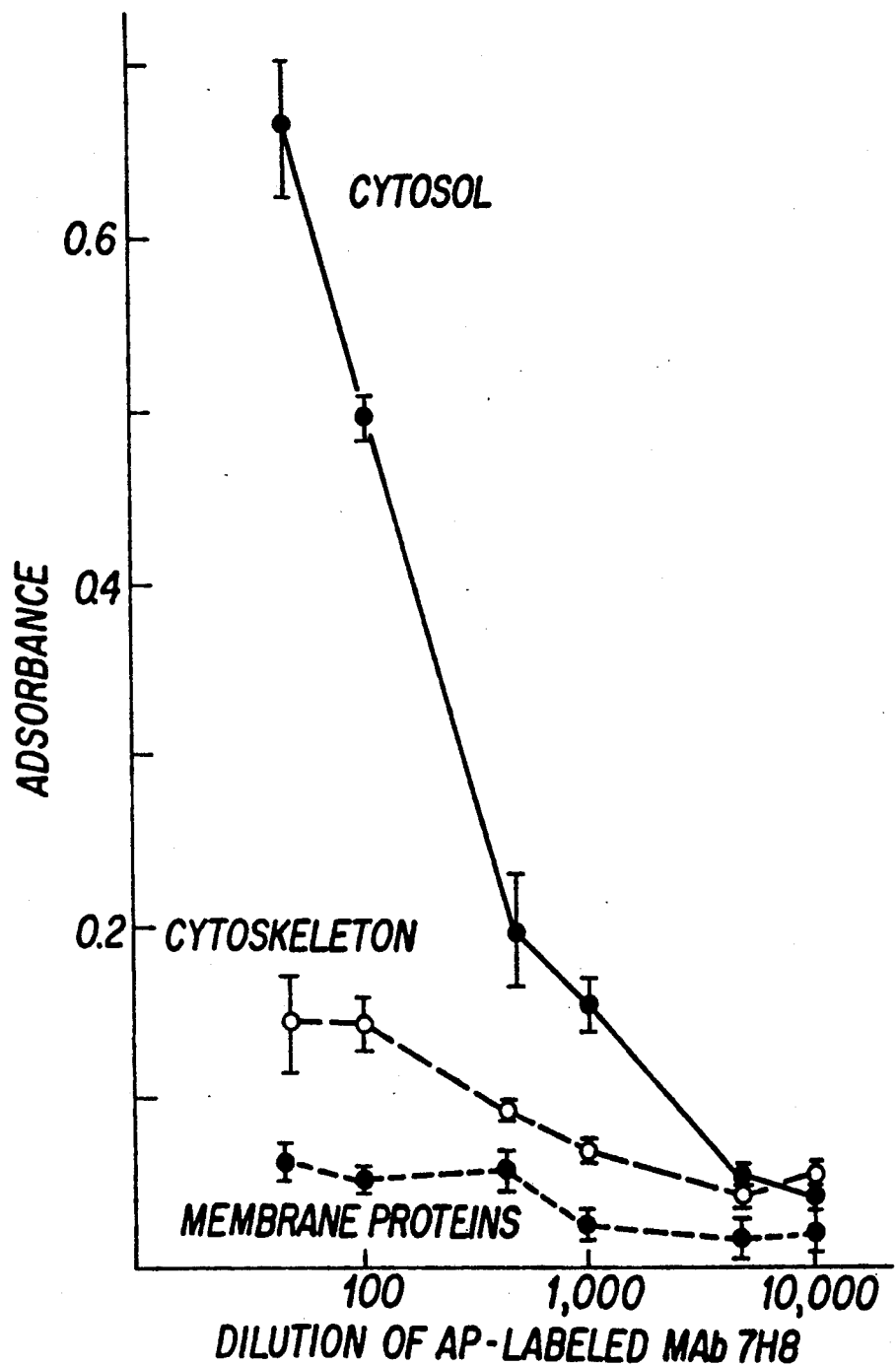
FIG. 3. Direct binding of alkaline-phosphatase (AP)-labeled MAb 7H8 to three extracts of *P. voelii*. Wells were coated with 100 ul of 1 mg of water-soluble parasite cytosol, Triton-X-100-extracted membrane proteins, or Triton-X-100-insoluble erythrocyte-parasite cytoskeletons per ml (the suspension was prepared in a tissue homogenizer before use). Antigen-coated wells treated with PBS served as the blank. In subsequent studies, the alkaline-phosphatase-labeled conjugate was used at a 1:500 dilution.

Initially, a direct-binding assay was used to titrate the preparation of alkaline-phosphatase-labeled MAb 7H8 and to determine if the antigen was water-soluble. In this assay, microtiter wells were treated with 100 ul of approximately 1 mg of *P. voelii* antigen extracts of either parasite cytosol, Triton-X-100-extracted membrane proteins, or Triton-X-100-insoluble cytoskeletons per ml. The results demonstrated that the labeled antigen bound preferentially to an antigen in the parasite cytosol (FIG. 3). In later studies, the conjugate was used routinely at a 1:500 dilution.

Figure 4A:
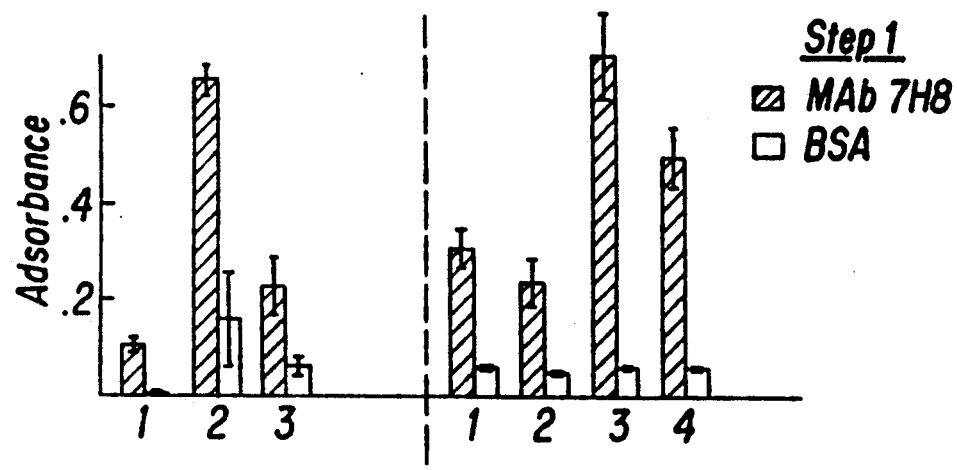
FIG. 4. Use of a two-sited assay for the detection of Ag-7H8 in extracts of *P. voelii* cytosol and plasma samples from mice with acute malaria. The upper portion shows that, in general, Ag-7H8 was captured by wells coated with MAb 7H8 but not with BSA. The exception was *P. voelii* extract 2. The lower portion demonstrates the heat-stable nature of Ag-7H8. The four antigen extracts on the left contained cytosol isolated from approximately (1) $10^7$, (2) $2.5 \times 10^7$, (3) $10^6$, and (4) $10^6$ Percoll-isolated, infected erythrocytes. The acute-phase plasma samples on the right were collected on days 5 (samples 1 and 3) and 6 (samples 2 and 3) after infection with 17XL *P. voelii* and on day 7 (sample 4) after inoculation with 17XNL *P. voelii*.Samples contained plasma pooled from 20 to 50 BALB/c mice.
Figure 4B:
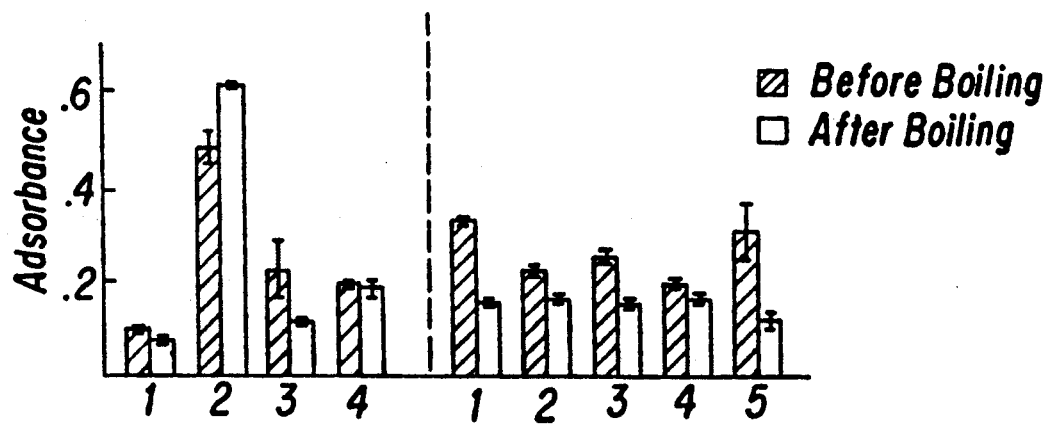

Next, a two-sited assay was attempted. In step 1 of this initial assay, wells were coated with 100 ug of partially purified MAb 7H8 at a 1-mg/ml concentration or with 3% BSA. Extracts of *P. voelii* or plasma samples from acutely infected mice were used as the source of the antigen in step 2, and a 1:500 dilution of alkaline-phosphatase-labeled MAb 7H8 was employed in step 3. The *P. voelii* antigen was usually captured by MAb-coated wells but not by wells coated with BSA (FIG. 4, upper left portion). However, when large amounts of Ag-7H8 were used (e.g., as a parasite extract 2), a substantial amount of reactivity was observed in BSA-coated wells. Thus, in the presence of high antigen concentrations, both captured and nonspecifically bound antigens were detected. These results demonstrated that *P. voelii* cytosol contains an antigen with at least two similar epitopes and that the antigen appears in acute-phase plasma.

Figure 5:
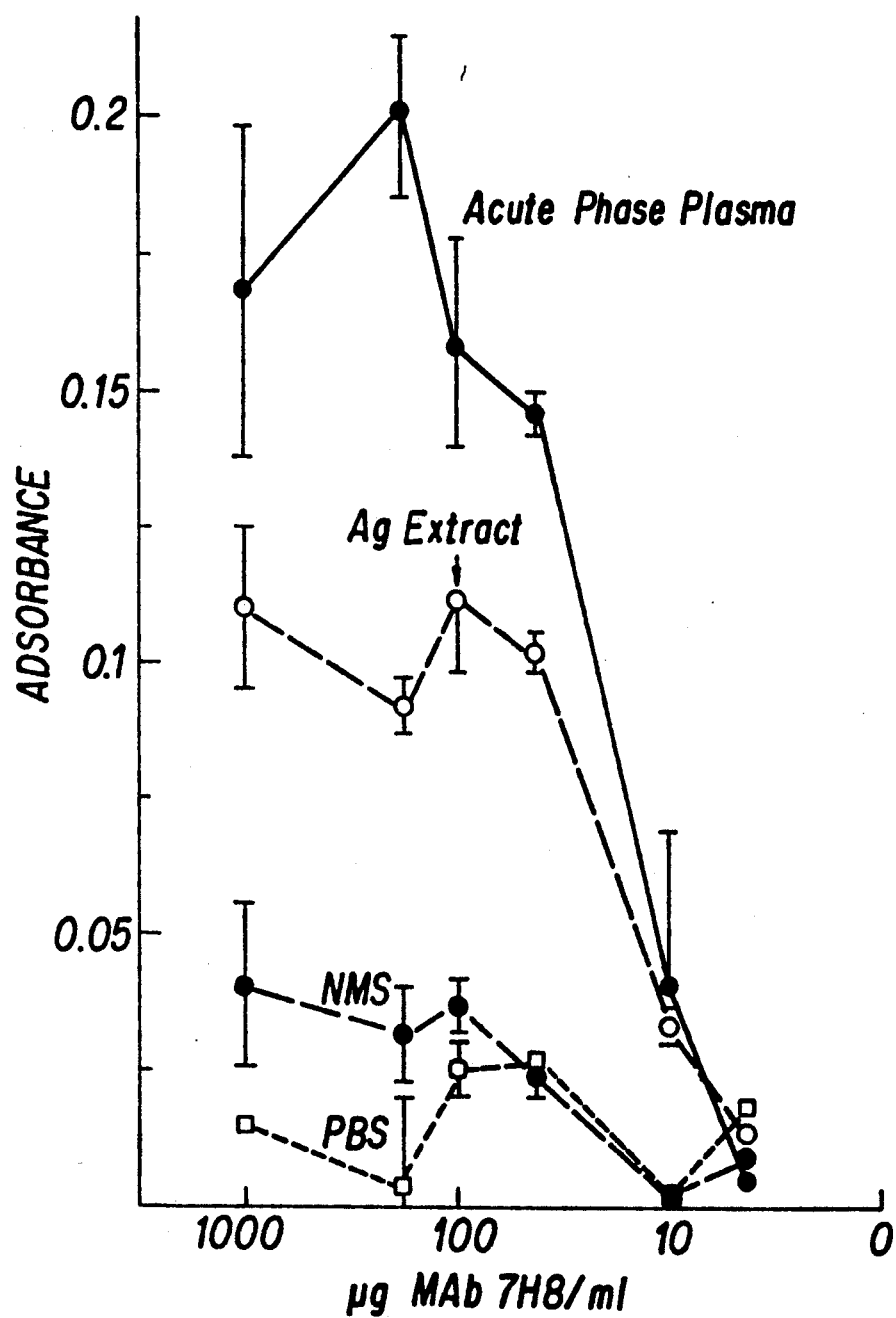
FIG. 5. Determination of the optimal amount of partially purified MAb 7H8 for application to microtiter wells. In step 1 microtiter wells were coated with various amounts of from 1 to 1,000 ug of partially purified MAb 7H8 per ml. PBS, normal mouse serum (NMS), acute-phase plasma samples from mice with 30% parasitemia, and *P. voelii* cytosol extract (Ag) ( 1 mg/ml) were diluted 1:1 with 3% BSA in PBS and used in step 2. A 1:500 dilution of alkaline-phosphatase-labeled MAb 7H8 was used in step 3. Results are expressed as means ±1 standard deviation for triplicate samples.

Aliquots from four parasite extracts and plasma samples from mice acutely infected with 17XL and 17XNL *P. voelii* were heated in a boiling water bath for 5 min to determine if the antigen detected in the two-sited assay is heat-stable. Paired samples of unboiled extract or plasma and the colorless supernatant from boiled samples were compared. Ag-7H8 could easily be detected after boiling (FIG. 4, lower half). However, the amount of reactivity was frequently diminished after boiling the samples, especially the sera. Finally, we determined the optimal amount of partially purified MAb to apply to the plate (step 1 of the assay). Accordingly, wells were coated with various amounts of MAb 7H8 (FIG. 5). When wells were coated with less than 10 ug/ml (i.e., 1 ug per well), they were unable to capture sufficient amounts of the antigen. Thus, in all subsequent experiments wells were coated with 100 ug of MAb 7H8 per ml.

In the development of the assay, ascites from two different clones of MAb 7H8 were used. Similar results were obtained for kinetics of reactivity and titration curves.

Detection of Ag-7H8 in Plasma Collected During *P. voelii* infection

Figure 6B:
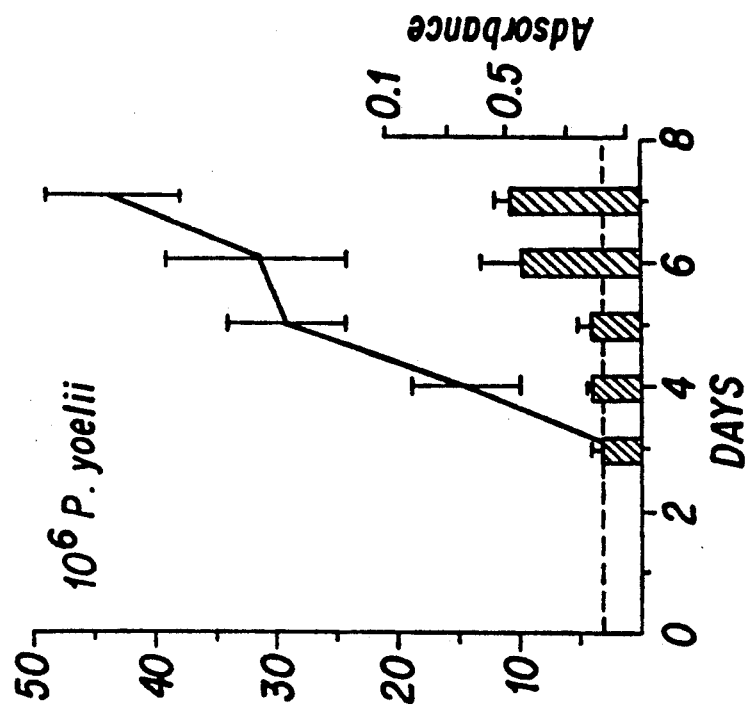
FIG. 6. Detection of Ag-7H8 in the serum of mice during 17XL *P. voelii* infection. Groups of 21 and 15 BALB/c mice were infected with $10^4$ and $10^6$ 17XL *P. voelii* parasites, respectively. Three mice in each group were bled out daily, and plasma samples from individual mice were pooled and examined in the two-sited assay. The left axis and ascending curve show the course of parasitemia (the mean±the standard error of the mean for three mice). The right axis and bars show results of the two-sited assay. Results are expressed as means ±1 standard deviation for triplicate samples. Normal BALB/c plasma samples (-------) were used as a control.
Figure 6A:
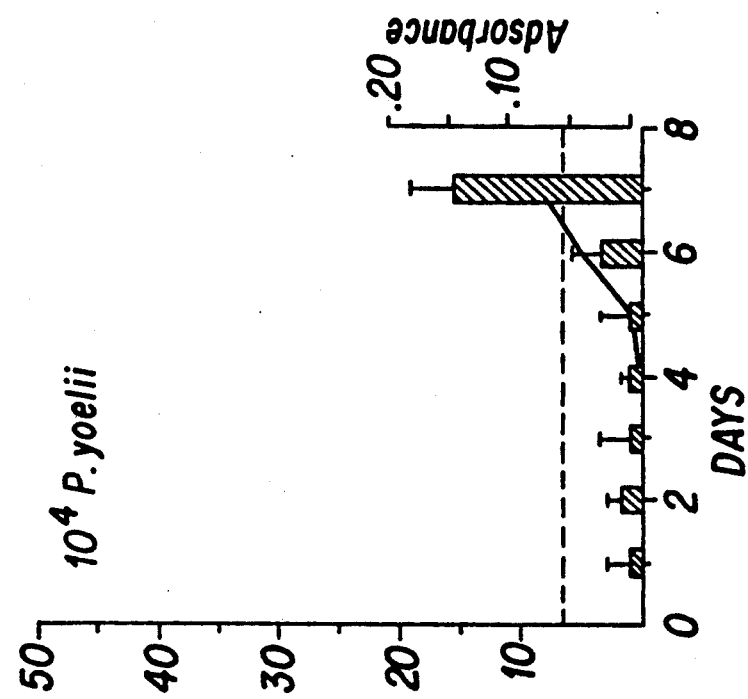

Plasma samples collected during the 17XL *P. voelii* infection in BALB/c mice were diluted 1:1 in 3% BSA in PBS and assayed for Ag-7H8. The results demonstrated that the antigen could be detected in plasma on days 6 and 7 after injection of $10^4$ and $10^6$ parasites, respectively (FIG. 6).

Figure 7A:
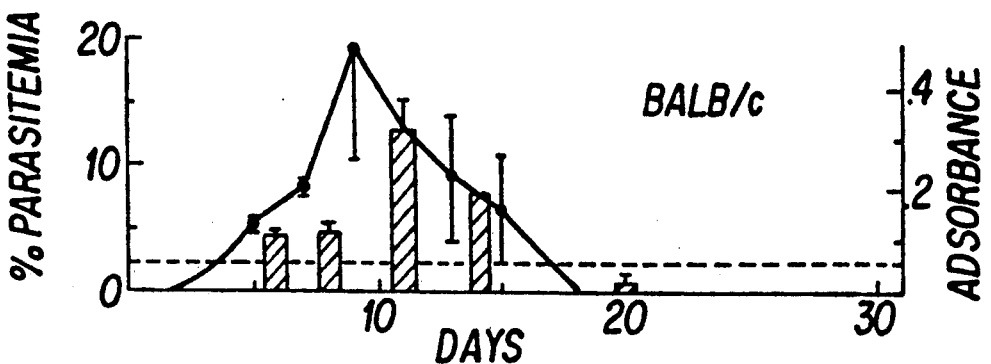
FIG. 7. Detection of Ag-7H8 in the plasma samples of various strains of mice infected with 17XNL strain of *P. voelii*. Groups of nine mice each were infected with $10^6$ 17XNL *P. voelii* parasites. Parasitemias (the left axis and ascending curves) are the mean for six to nine animals. Blood samples, collected from three mice on the days indicated, were pooled and assayed in the two-sited assay. Results (the right axis and bars) are expressed as means ±1 standard deviation for triplicate samples. Results for all C57B1/6 (B6) congenics were virtually identical, so only one is shown.
Figure 7B:
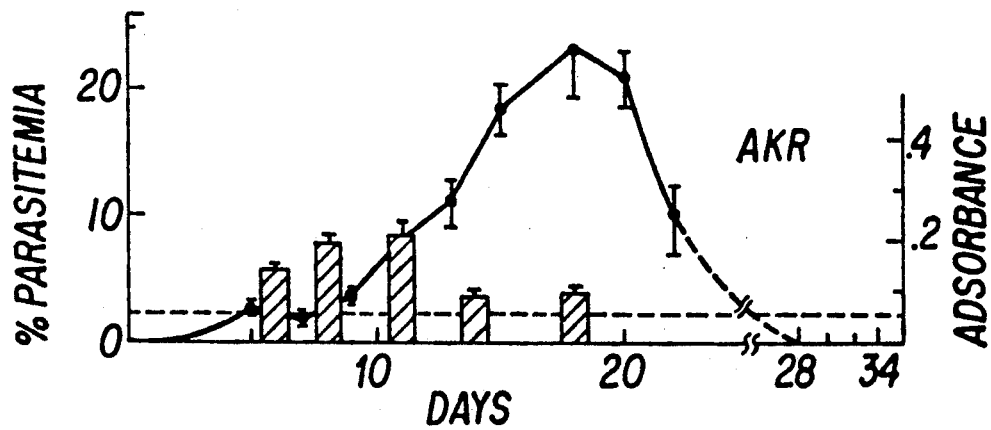
Figure 7C:
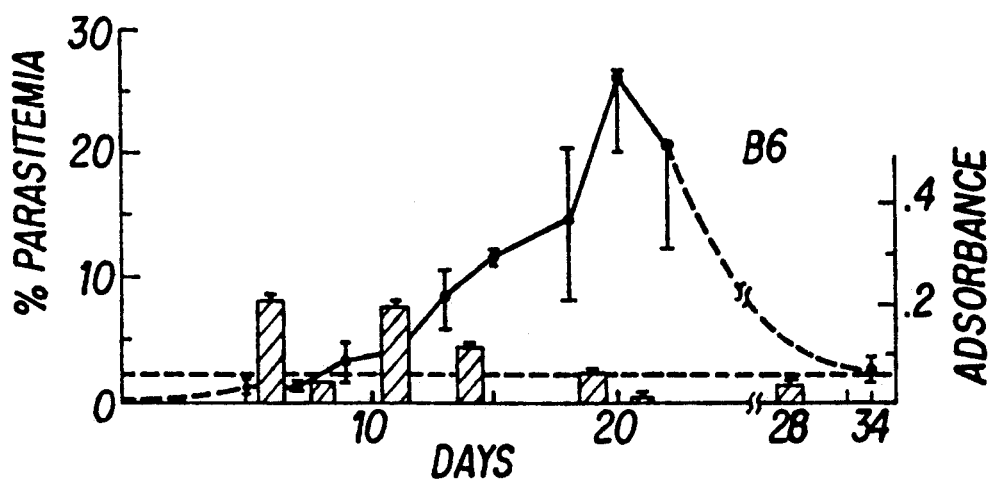

Various inbred strains of mice were infected with $10^6$ 17XNL *P. voelii* parasites. Blood samples, collected from three mice on the days indicated, were pooled and assayed. Results demonstrated the presence of Ag-7H8 in the plasma samples of BALB/c, AKR/J, C57BL/6, and C57BL/6 (H-$2^k$) mice between days 6 and 14 of infection, with amounts peaking at day 11 (FIG. 7). The appearance of Ag-7H8 in plasma corresponded to the onset and early stages of infection and did not parallel the course of parasitemia.

DISCUSSION

The present inventor identified an antigen (7H8) that circulates in the peripheral blood during the early stages of *P. voelii* infection. This antigen is produced by the parasite and has a major high-molecular-weight component of 117,000 to 120,000 as determined by both immune precipitation of [$^{35}$S]methionine-labeled proteins and by Western blot analysis. In addition to the major band detected by the two assays, several lesser bands can be identified, including bands of 200,000; 65,000 to 75,000; and 45,000. Thus, it appears that the epitope is on molecules of diverse sizes. The identification of the same epitope on molecules of different sizes is not unusual. For example, the dominant protein on the surface of malarial merozoites in *P. voelii* has a major band of 230,000 plus lesser bands of 197,000, 160,000, 151,000, 126,000, 90,000, 56,000, and 28,000. Holder A.A., and R.R. Freeman, *Nature* 294:361-364 (1981). MAb 8B11 (FIG. 2) identifies this protein. It is not yet clear if the lesser components recognized by MAb 7H8 are aggregates, breakdown products, or true alternative forms of the antigen.

Ag-7H8 can be detected in cytosol extracts of parasites and acute-phase plasma samples after boiling for 5 min (FIG. 4). However, the amount of activity is reduced after boiling, especially when plasma samples from acutely infected mice are used. The reason for diminished activity could be due to: (i) a portion of Ag-7H8 becoming trapped in the protein aggregate formed during boiling (which is considerably greater in plasma than in extracts); (ii) some of the molecules (i.e., bands) that possess epitope 7H8 being thermostable, whereas others are not; or (iii) the basic structure of the molecule being altered by heating but the epitope recognized by MAb 7H8 being only moderately affected. The last possibility could result in a lowered-affinity interaction between the MAb and the epitope. However, the data shown in FIG. 4 support the conclusion that Ag-7H8 in parasite extracts and a portion of the antigen in plasma samples are stable to boiling for 5 min.

Ag-7H8 appeared in plasma samples 6 to 7 days after infection (FIG. 6 and 7), regardless of the inoculation dose in both lethal and nonlethal *P. voelii* infections. At that time, the antigens detected were probably in the free state and not in immune complexes, as only low levels of antibodies were being produced. As the infection progressed, Ag-7H8 was detected up to day 14. It is possible that during this time antibodies were produced against it, resulting in the clearance of the antigen from the circulation. The kinetics of antigenemia were similar in BALB/c, AKR, and C57BL/6 mice, although the courses of parasitemia differed greatly in these inbred strains (FIG. 7). Thus, the kinetics of antigenemia correlate with the initial stages of infection and not the level of parasitemia.

The above explanation of the clearance of Ag-7H8 is based on the assumption that antibodies are produced against it during the early stages of infection. This, however, may not be true. In the last several years, mice have been infected with the 17XL and 17XNL strains of P. voelii, their spleens removed at various times after infection, and these tissues used for hybridoma production. Only one (7H8) of two hundred MAbs produces the pattern of fluorescence described here, suggesting that Ag-7H8 might be a weak immunogen. In addition, careful examination of SDS-PAGE results (FIG. 2) reveals that, although approximately equal amounts of the upper 150- and 120-kDa bands are immune-precipitated by MAb-7H8, sera from immune mice contain antibodies to the upper two proteins of the triplet (150 and 136 kDa) but not to the third (120 kDa) or the smaller bands. This result has been observed in other immune precipitation studies with hyperimmune serum and sera collected on day 11 of the primary infection. That is, antibodies to the lower band (120 kDa and the smaller proteins with this epitope) are rarely, if ever, found in immune serum. Thus, this antigen may have low immunogenicity.

Is Ag-7H8 secreted into sera, released during erythrocyte rupture and parasite reinvasion, or produced by degenerating parasites? The pattern of fluorescence produced by MAb 7H8 is consistent with that of a secreted protein and appears similar to that reported for the S antigen of P. falciparum. Coppel, R.L, et al., Nature 306:751-756 (1983); McGregor, I.A., et al., Lancet1:881-884 (1968). Ag-7H8 is absent in the ring stage parasites and appears during early trophozoite formation (FIG. 1). The antigen appears to be located primarily in the space external to the parasite and internal to the erythrocyte membrane. The finding that the antigen remains in discrete granules when the erythrocyte membrane is ruptured but when the parasite membrane remains intact supports the idea that the antigen is transported packaged in vesicles through the erythrocyte and then either stored within the erythrocyte cytoplasm or actively secreted into the serum. Attempts to make this distinction have not been successful.

Circulating antigens in sera could have a role in immunosuppression, immune protection, and immune-complex formation. Recently, Saul et al., Parasite Immunol 6:39-50 (1984); Saul et al., Parasite Immunol. 7:587-594 (1986), showed that a MAb against P. falciparum S antigens could block parasite growth in vitro. The mechanism of this MAb is unclear. Accordingly, Ag-7H8 could play several immunologic roles. The results from 17XNL P. voelii studies suggest that Ag-7H8 may be involved in immune protection or immune-complex formation (FIG. 7). Studies are in progress to elucidate the role of this antigen.

A two-sited assay was developed for detecting Ag-7H8. The sensitivity of the assay was difficult to ascertain, but antigens could be detected circulating in the blood when the parasetemias were <2% (FIG. 7). Technical difficulties encountered with the two-sited assay for detecting Ag-7H8 were minimal However, as the amount of Ag-7H8 in extracts of malarial parasites increased, the amount of color development in wells not coated with MAb 7H8 (i.e., the BSA used in step 1) increased. This suggests that during the overnight incubation period, some of the antigens bound directly to the plate. It appears that in samples containing large amounts of Ag-7H8, both captured and nonspecifically bound antigens were detected. In addition, it is possible that Ag-7H8 was not detected beyond day 14 because antibodies produced by the host interfered with the assay.

Since Ag-7H8 is in P. voelii, P. berghei, and P. falciparum parasites, it is likely that this assay has general application for the detection of this circulating malarial antigen. Preliminary studies show that Ag-7H8 can be detected in plasma samples of individuals living in The Gambia and Nigeria with acute P. falciparum infections.

Thus, identification of a P. voelii antigen that shares many characteristics with S antigens in P. falciparum may provide us with an animal model system for determining if this family of high-molecular-weight, water-soluble, heat-stable antigens found in sera during acute malaria plays a role in immune protection, immunosuppression, or immune complex formation.

EXAMPLE 2

Characterization of Pf93 Antigen Released into Sera During Malarial Infection.

Figure 9:
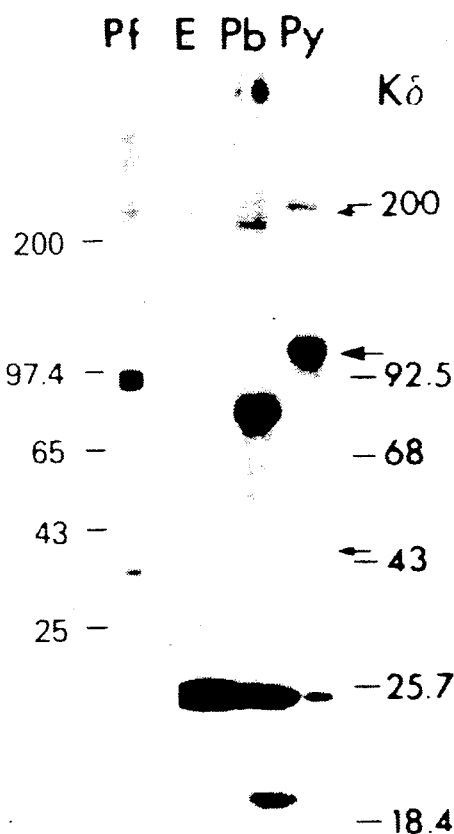
FIG. 9. Western blot analysis of antigen 7H8 in *P. berghei* (Pb), *P. voelli* (Py), and *P. falciparum* (Pf).
Figure 10:
FIG. 10. Schematic diagram showing production of a portion of antigen Pf93 in the lambda gt11/*E. coli* Y1090 system.

FIG. 8 shows the indirect immunofluorescence pattern produced by normal mouse serum (negative control), immune serum on rings, trophozoites and schizonts, and MAb 7H8 on P. voelli and P. falciparum. Review of the figure shows that the antigen is present in "packets" in the erythrocyte cytoplasm. The parasite itself is basically negative. Western Blot analysis, (FIG. 9), shows that the antigen has a molecular weight of $M_r$ 120,000 in P. voelli, about 80,000 in P. berghei and 93,000 in P. falciparum. This is thus termed the 7H8 family of proteins or, pan-malarial proteins, because they all contain a common epitope detected by MAb 7H8, and the antigen in P. falciparum, Pf93. Pf93 is a new, previously undescribed Ag (FIG. 10). We have isolated lambda gt11 phage that carry a DNA insert coding for the segment of Pf93 that carries the 7H8 epitope. It codes for a protein about Mr 13,000 or about 14% of the total protein. The DNA has been sequenced and the protein sequence deduced. The peptide containing the 7H8 epitope does not have tandem repeats. Comparison with two other P. falciparum antigens known to be present in sera shows that there is no sequence homology with either the $M_r$ 220,000 S-Ag identified by Coppel, Anders et al. of the Eliza Hall Institute or the secreted histidine-rich protein described by Wellems and Howard (PfHRP-2). In addition, DNA coding for Pf93 does not cross-hybridize with the gene coding for the 185-195 glycoprotein on the surface of merozoites or its breakdown fragments including the Pf83 exoantigen.

Production and Release of Pf93

Figure 11:
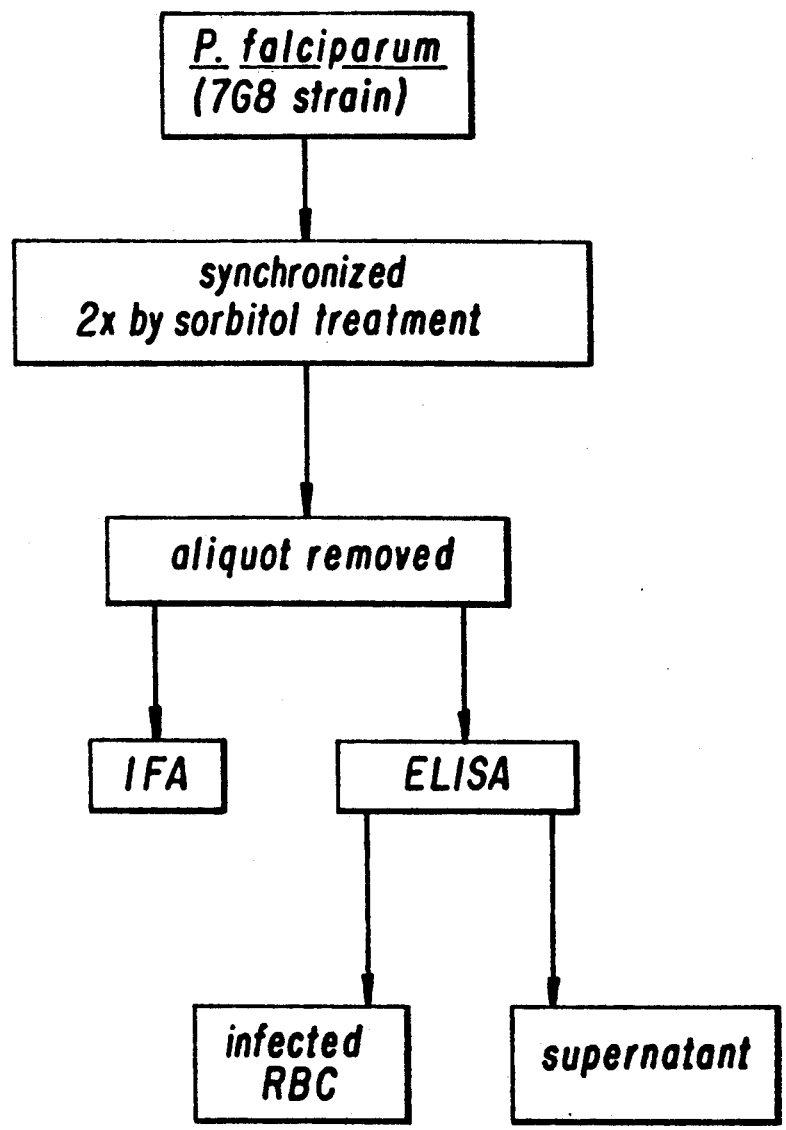
FIG. 11. Flow diagram showing steps of production and release of Pf93 in *P. falciparum*.
Figure 12:
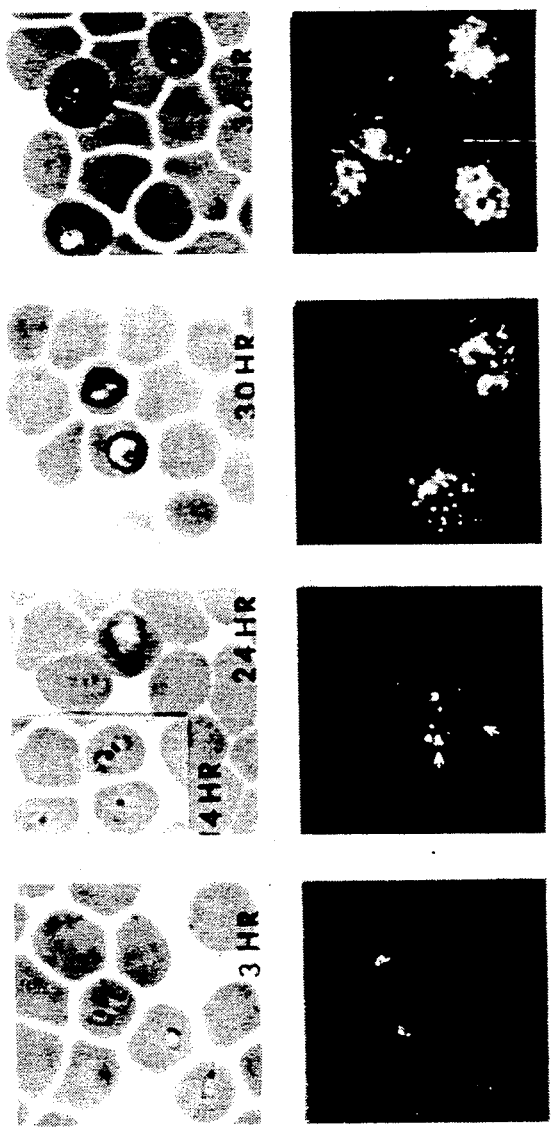
FIG. 12. IFA analysis of course of Pf93 production after RBC infection.

P. falciparum parasites of the 7H8 strain were synchronized twice by sorbitol treatment to remove mature parasites, and then cultured in vitro at 1.2% parasitemia (FIG. 11). Aliquots were removed, and smears made for IFA analysis and aliquots of supernatants and cells were collected and analyzed by ELISA for Pf93. By IFA analysis (FIG. 12), we found that in samples obtained at 3 hours, when the parasites were rings (about 3-11 hours after merozoite invasion), discrete areas of fluorescence could be seen within the parasite itself. By as early as 6 hours later, but definitely by 24 hours when the parasites were early trophozoites, discrete packets of fluorescence were seen in the erythrocyte cytosol. By 30 hours a large number of granules were observed with the whole cell becoming full of granules in mature trophozoites. Some granules were still seen in schizontsegmenters. It should be noted that equivalent magnification and photographic enlargement were used in all photos. Thus, it appears that the antigen is in packets within in rings and moves into the erythrocyte cytosol during the trophozoite stage.

EXAMPLE 3

Two-Sited Assay using MAb 7H8

Figure 13:
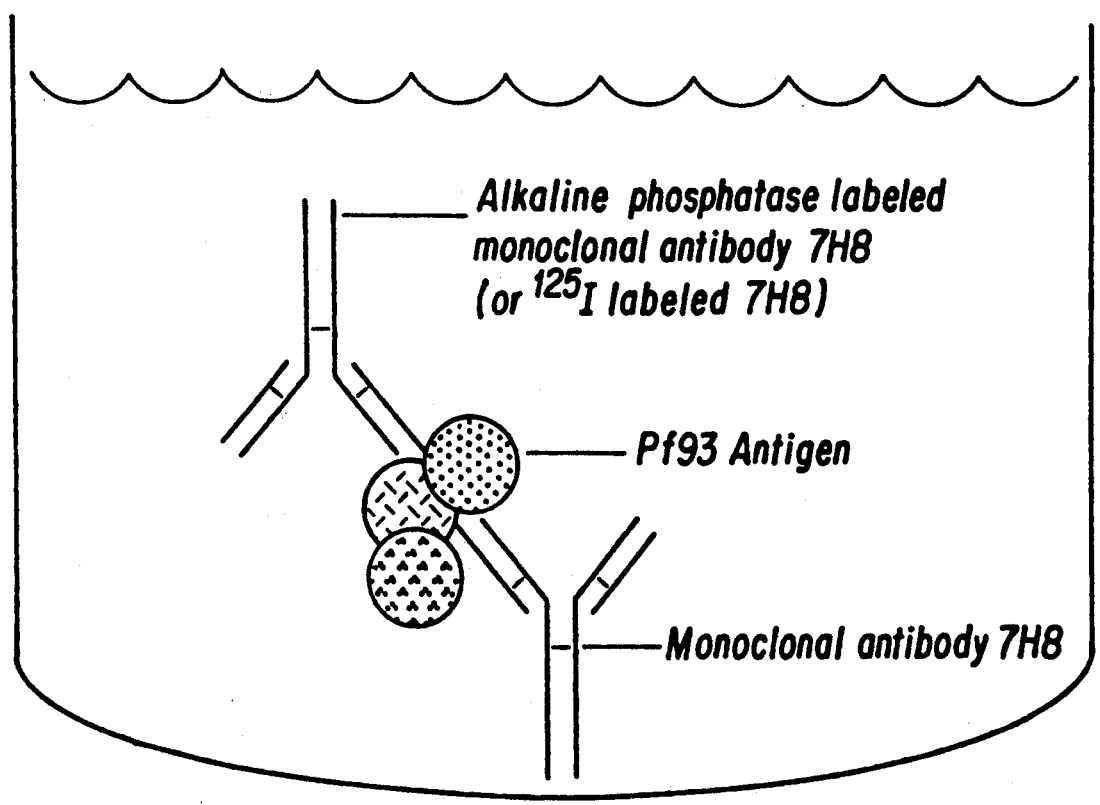
FIG. 13. Schematic diagram showing two-sited assay using MAb 7H8.
Figure 14:
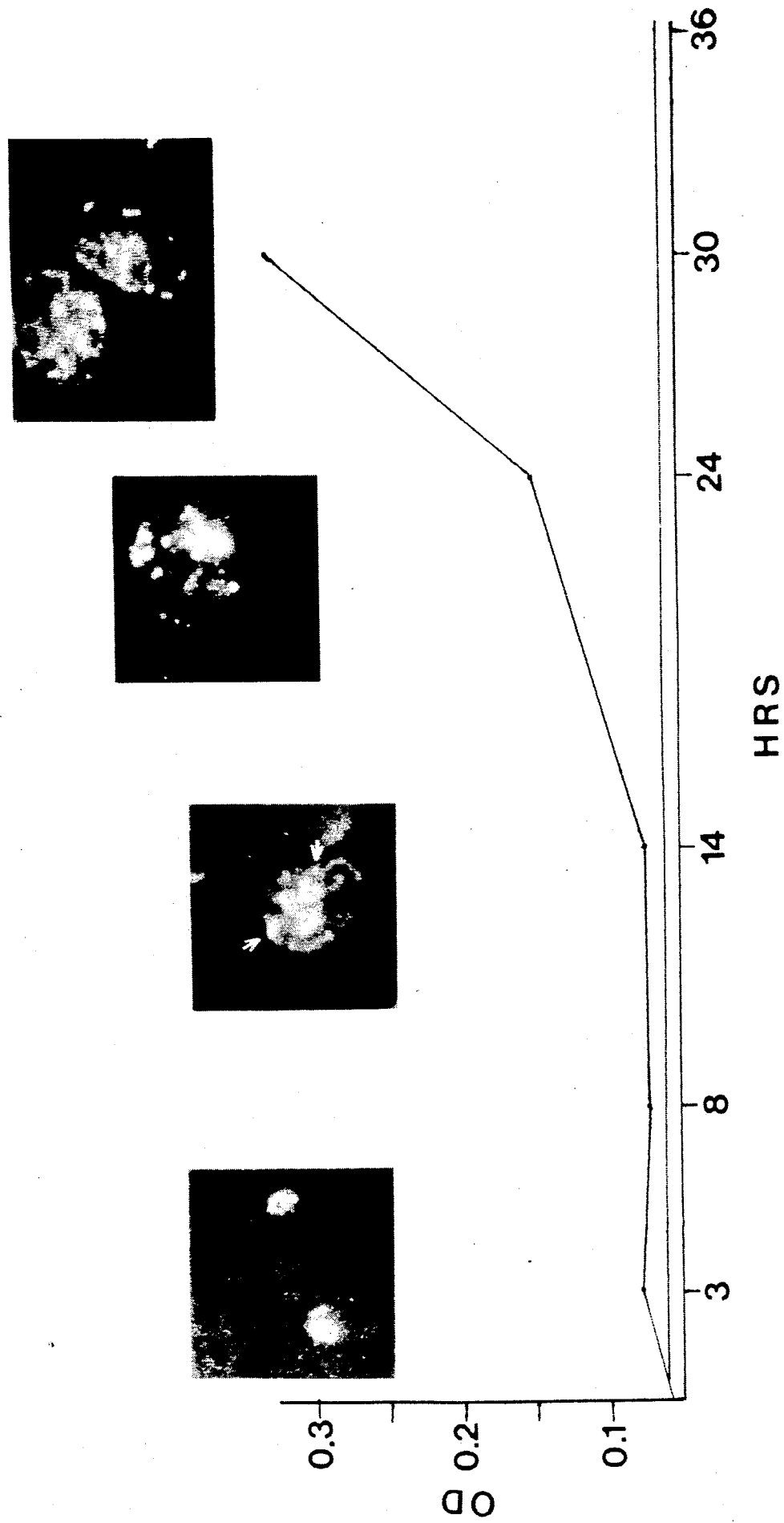
FIG. 14. Time course of antigen release from infected RBC's determined by two-sited assay using MAb 7H8.
Figure 15:
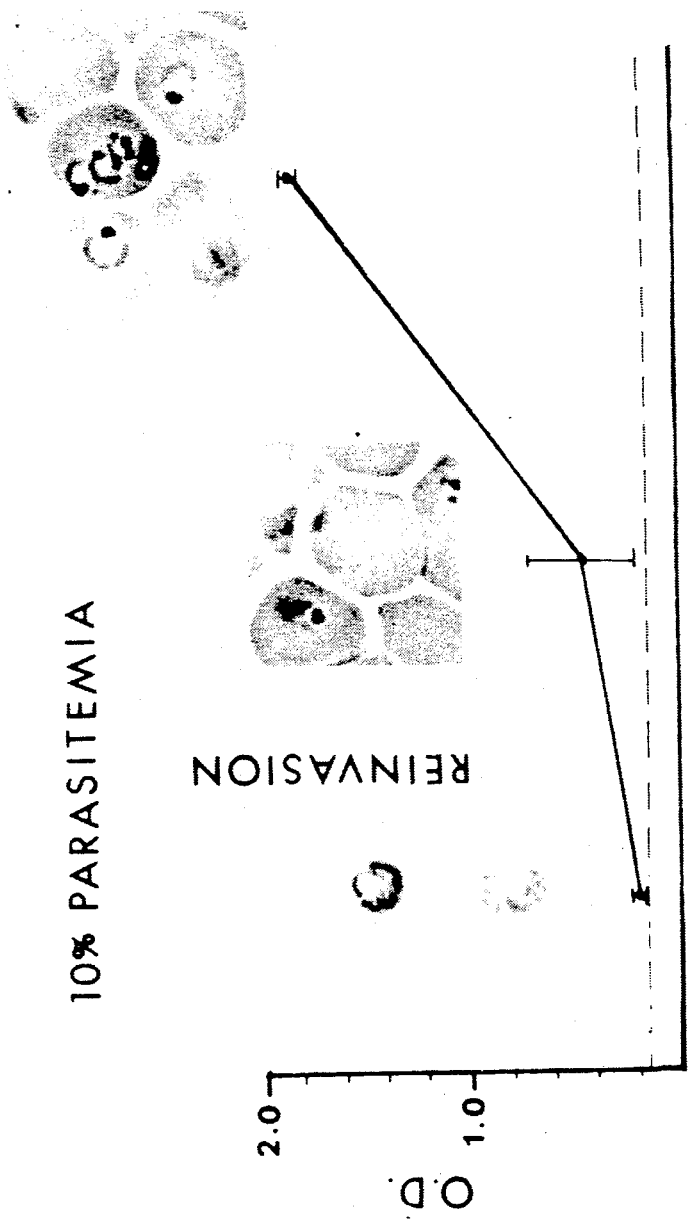
FIG. 15. Antigen release following reinvasion of RBC's determined by two-sited assay using MAb 7H8.
Figure 17:
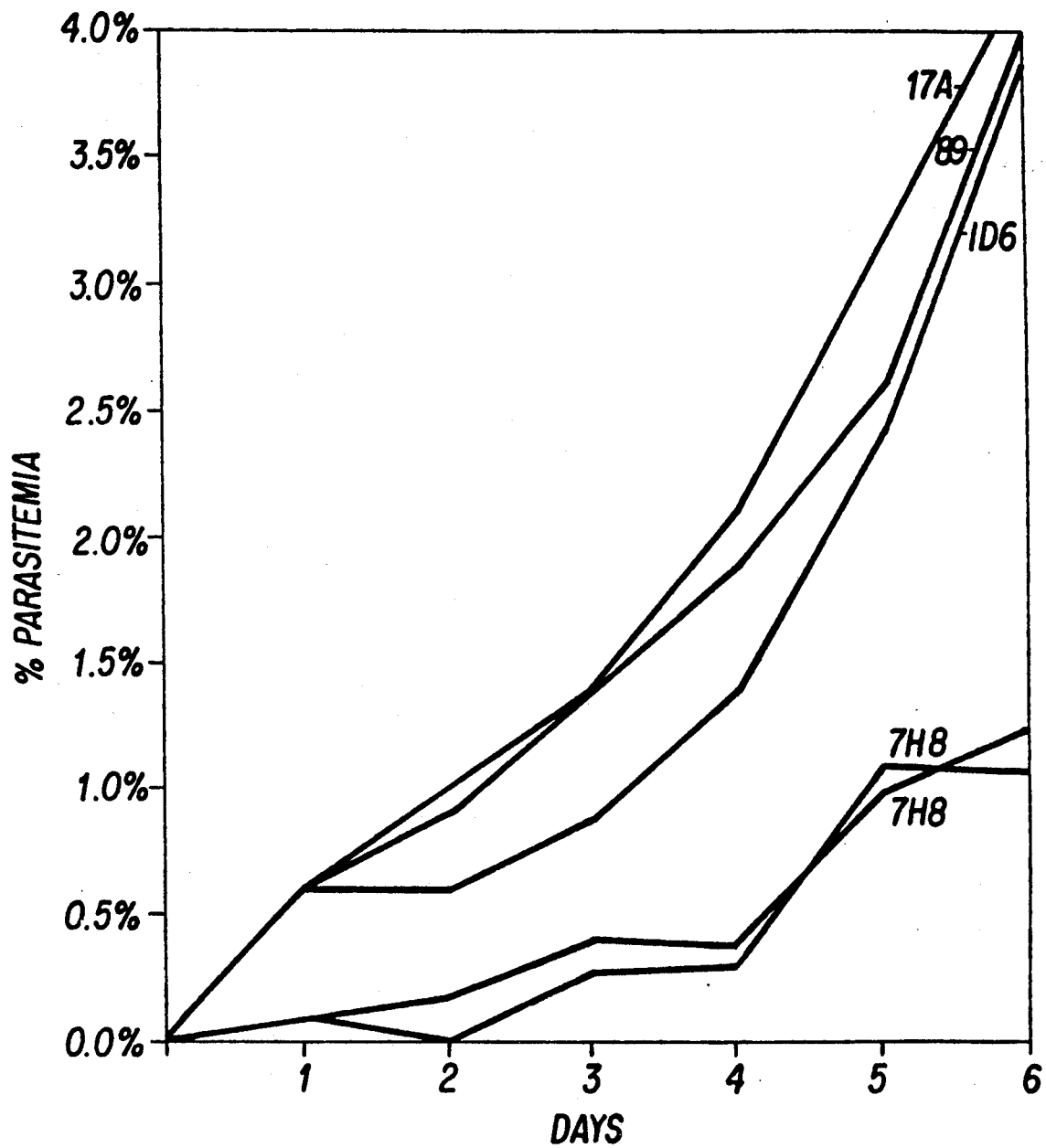
FIG. 17. *In vitro* inhibition of merozoite invasion in human erythrocytes by MAb 7H8.

Because of the general pattern of fluorescence it seemed possible that the antigen could be secreted from the parasite prior to schizont rupture. To determine this, supernatants were assayed in a two-sited assay (FIG. 13). Wells were coated with MAb 7H8, blocked, and 100 ul of supernatant was applied, followed by alkaline phosphatase-labeled 7H8 and substrate. The assay was performed several times with slightly varying results, but the general trend was similar (FIGS. 14 and 15). In the two-sited assay, increase in O.D., indicating the presence of the antigen, was noted at 24-30 hours with levels increasing until schizogony. At that time cultures were diluted to preserve the growth of the parasites. However, there did not appear to be a major burst of antigen release following rupture. Following re-invasion, such that there was a 10% parasitemia, large amounts of Ag were found in the supernatant during parasite growth. These data are consistent with the release of Ag prior to schizont rupture.

EXAMPLE 4

Detection of Pf93 in Human Sera

Figure 16:
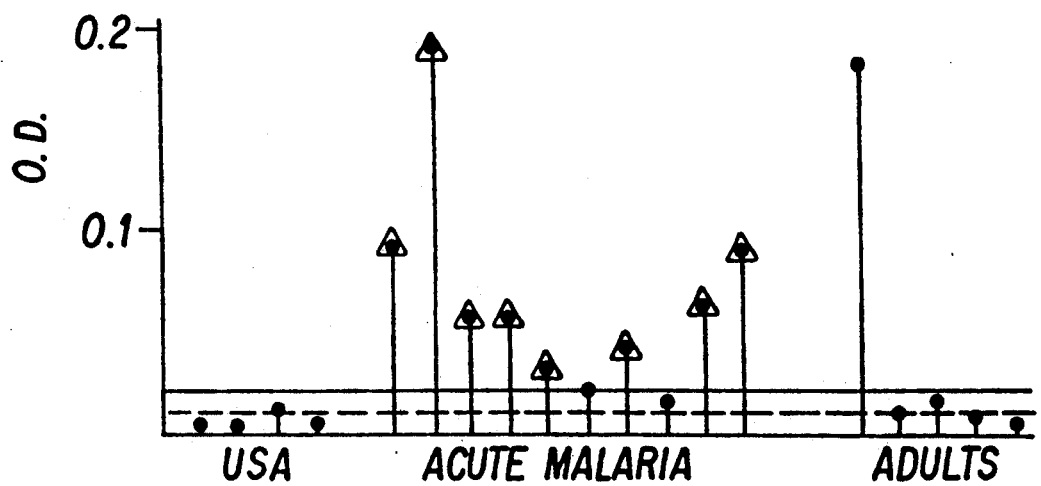
FIG. 16. Detection by two-sited assay using MAb 7H8 of antigen Pf93 in sera from individuals uninfected and acutely infected with *P. falciparum*.

Using sera collected from Nigerian individuals who were slide-positive for falciparum malaria, eight to ten individuals had detectable levels of Ag Pf93 in their blood (FIG. 16). Normal Americans and known negative Africans were negative in this two-sited assay. This demonstrates that antigen Pf93 circulates in human sera during acute malaria infection.

EXAMPLE 5

In Vitro Inhibition of Merozoite Invasion by MAb 7H8

Figure 18:
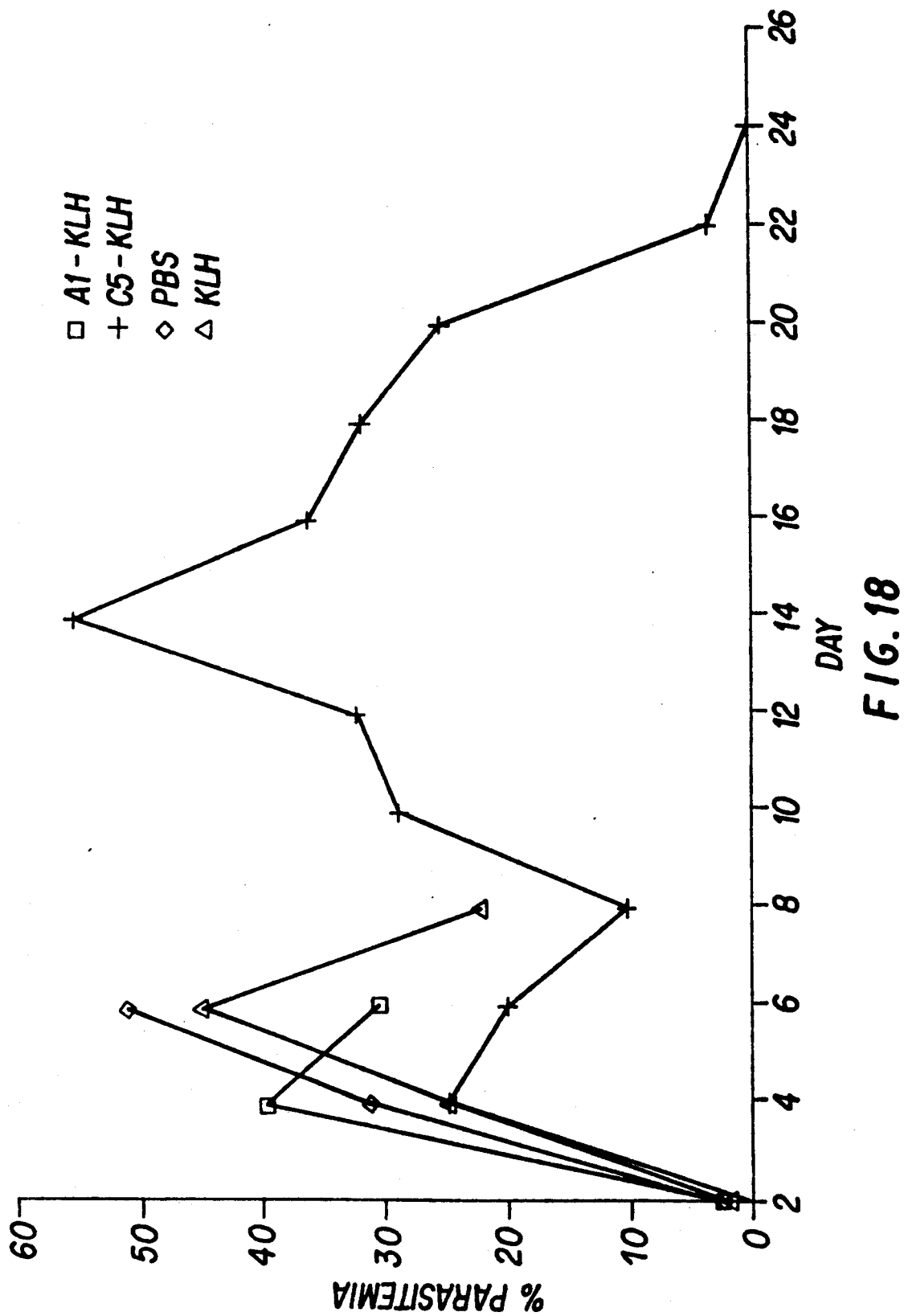
FIG. 18. Graph showing reduced parasitemia in 17XNL *P. voelli* malaria-challenged BALB/c mice immunized with anti-idiotypic antibody to MAb 7H8.

We tested the effect of MAb 7H8 on P. falciparum growth in vitro (FIG. 18). In three studies, MAbs purified from different clones of 7H8 were added at 1 mg/ml to cultures of P. falciparum NF54 in human erythrocytes. Cultures were 0.1% at the start and reached over 5% in the presence of control MAbs by day 6, but significantly lower parasitemias were observed in the presence of MAb 7h8. Control MAbs bind to (i) an antigen found at the apical end of merozoites, (ii) the histidine-rich knob-associated protein, and (iii) HRP-2 which is secreted by P. falciparum parasites. Thus, Abs to an epitope conserved in malarial parasites, i.e., Abs to the 7H8 epitope, have the ability to alter parasite growth in vitro.

EXAMPLE 6

Production of Monoclonal Anti-idiotypic Abs

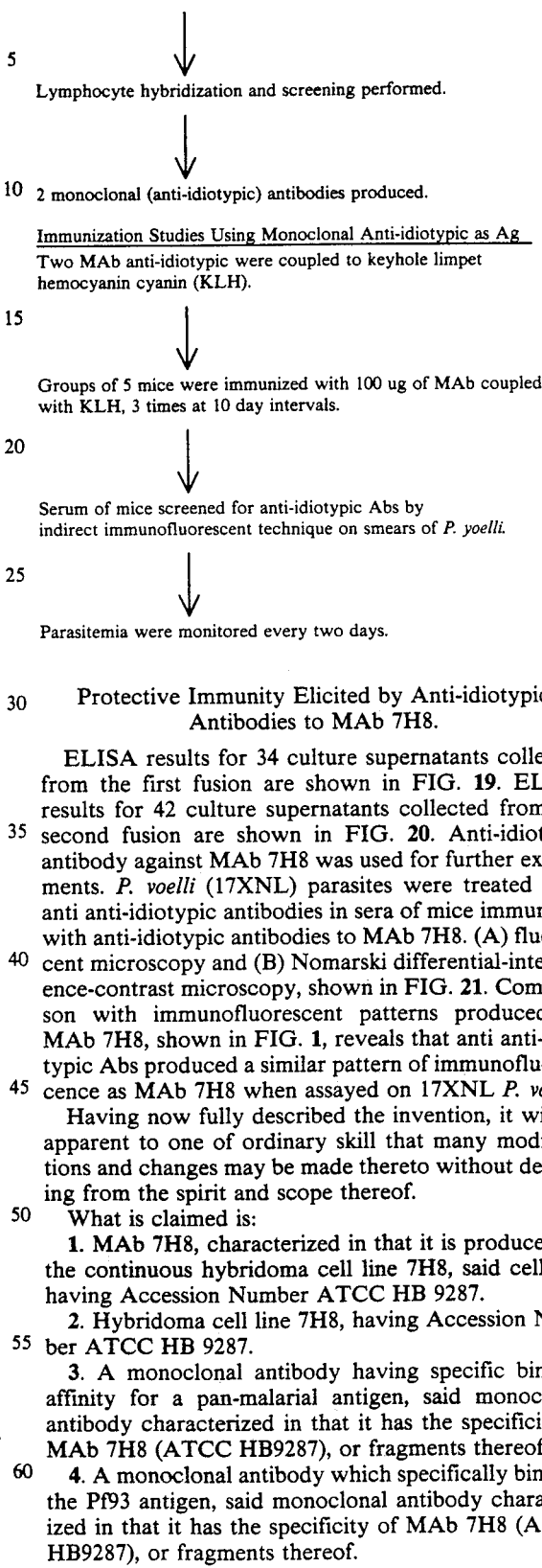

Protective Immunity Elicited by Anti-idiotypic Antibodies to MAb 7H8.

Figure 19:
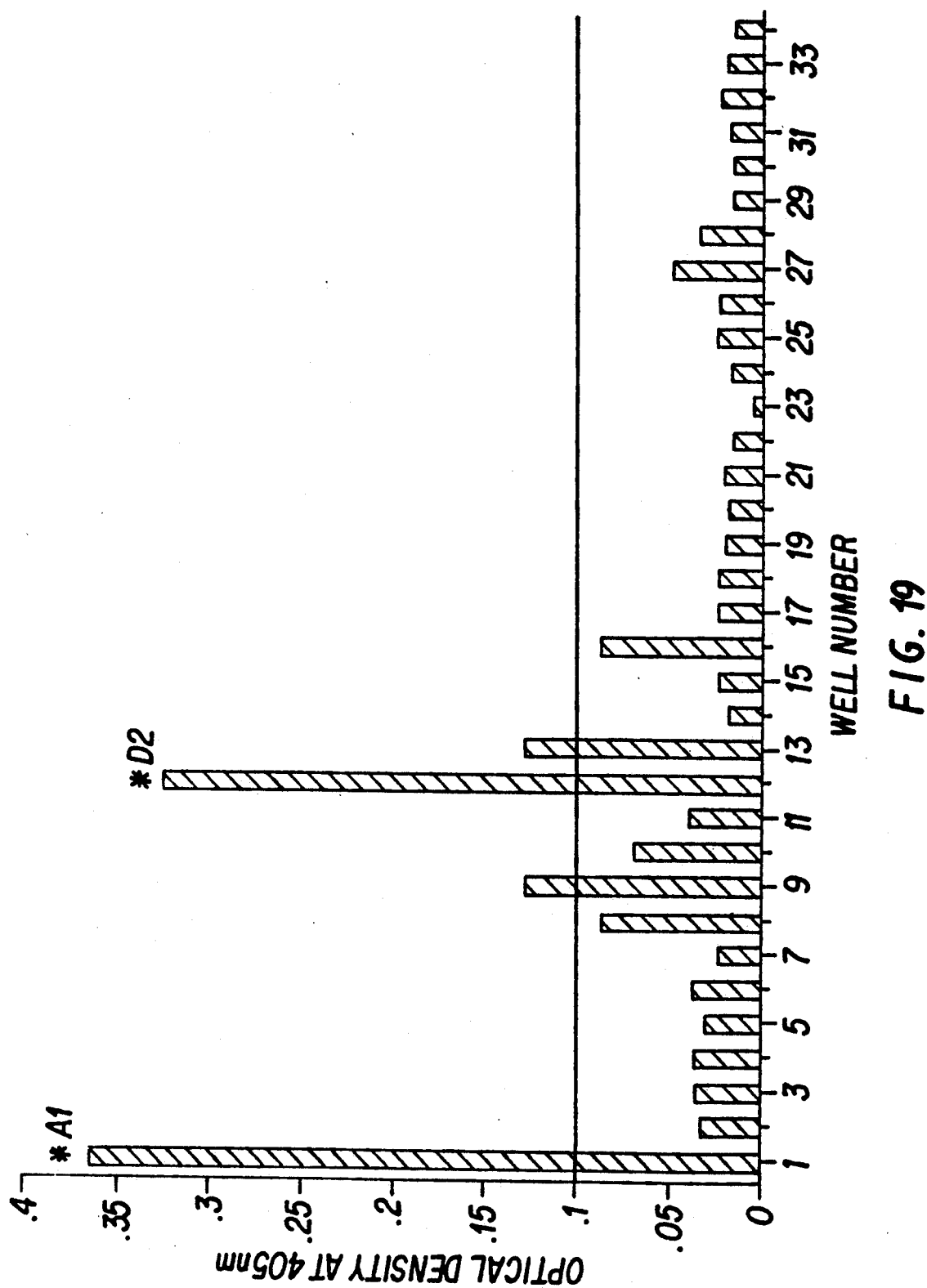
FIG. 19. ELISA of first fusion culture supernatants for anti-idiotypic antibodies to MAb 7H8. The asterisk denotes ELISA-positive culture containing antibody against MAb 7H8. (Horizontal line=25% of maximum specific binding.)
Figure 20:
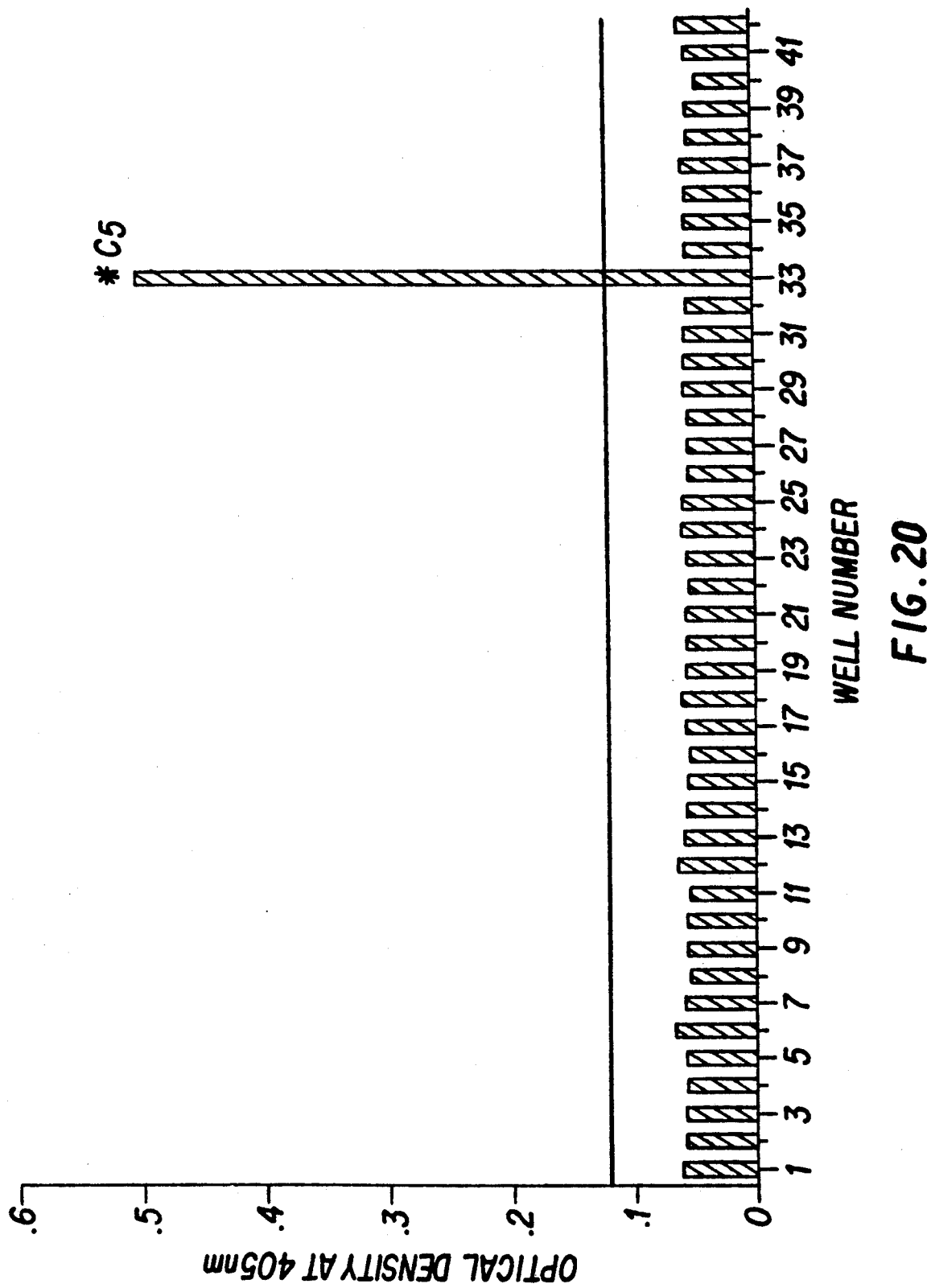
FIG. 20. ELISA of second fusion culture supernatants for anti-idiotypic antibodies to MAb 7H8. The asterisk denotes ELISA-positive culture containing antibody against MAb 7H8. (Horizontal line=25% of maximum specific binding.)
Figure 21A:
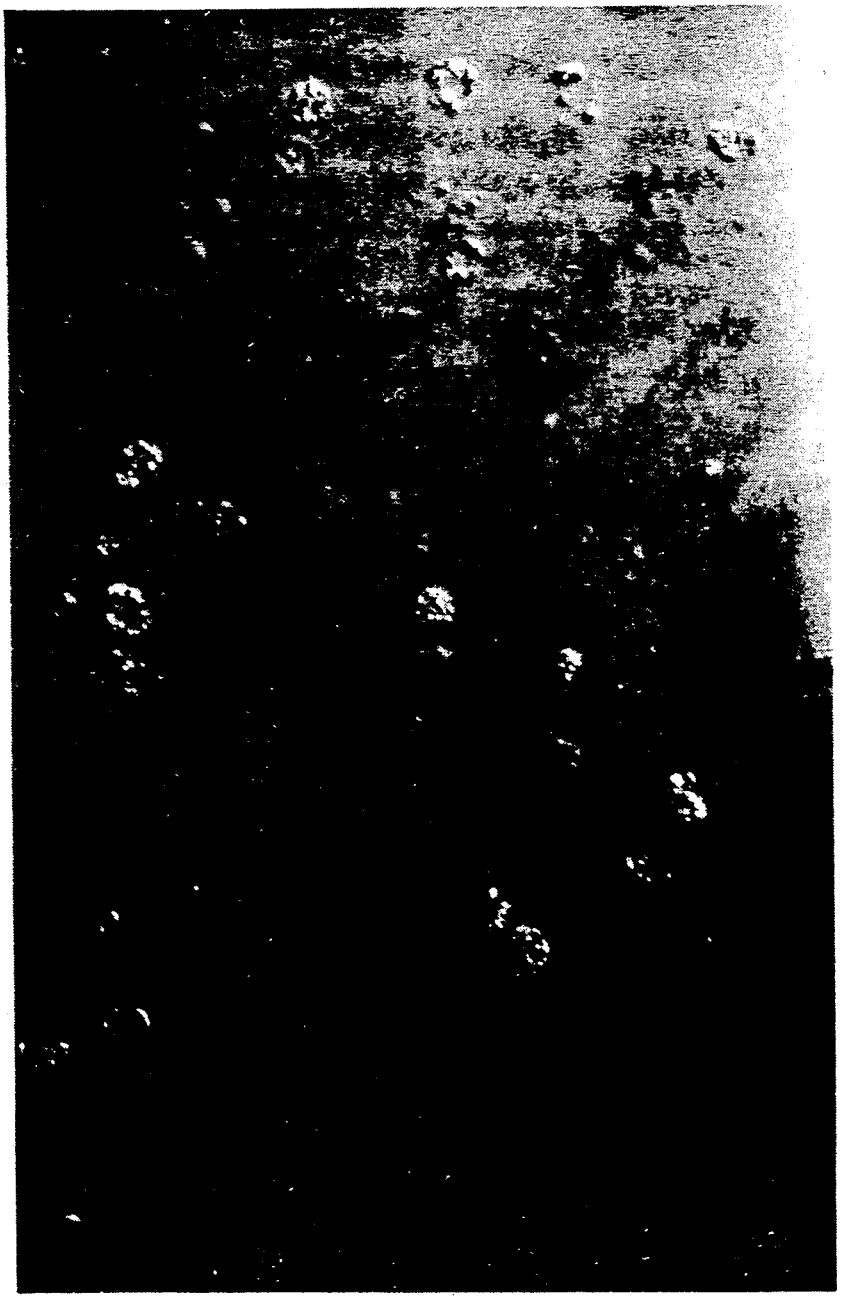
FIG. 21. Visualization of *P. voelli* 17XNL parasites treated with anti anti-idiotypic antibodies in sera of mice immunized with anti-idiotypic antibodies to MAb 7H8. (A) Fluorescence microscopy. (B) Nomarski differential interference contrast microscopy.
Figure 21B:
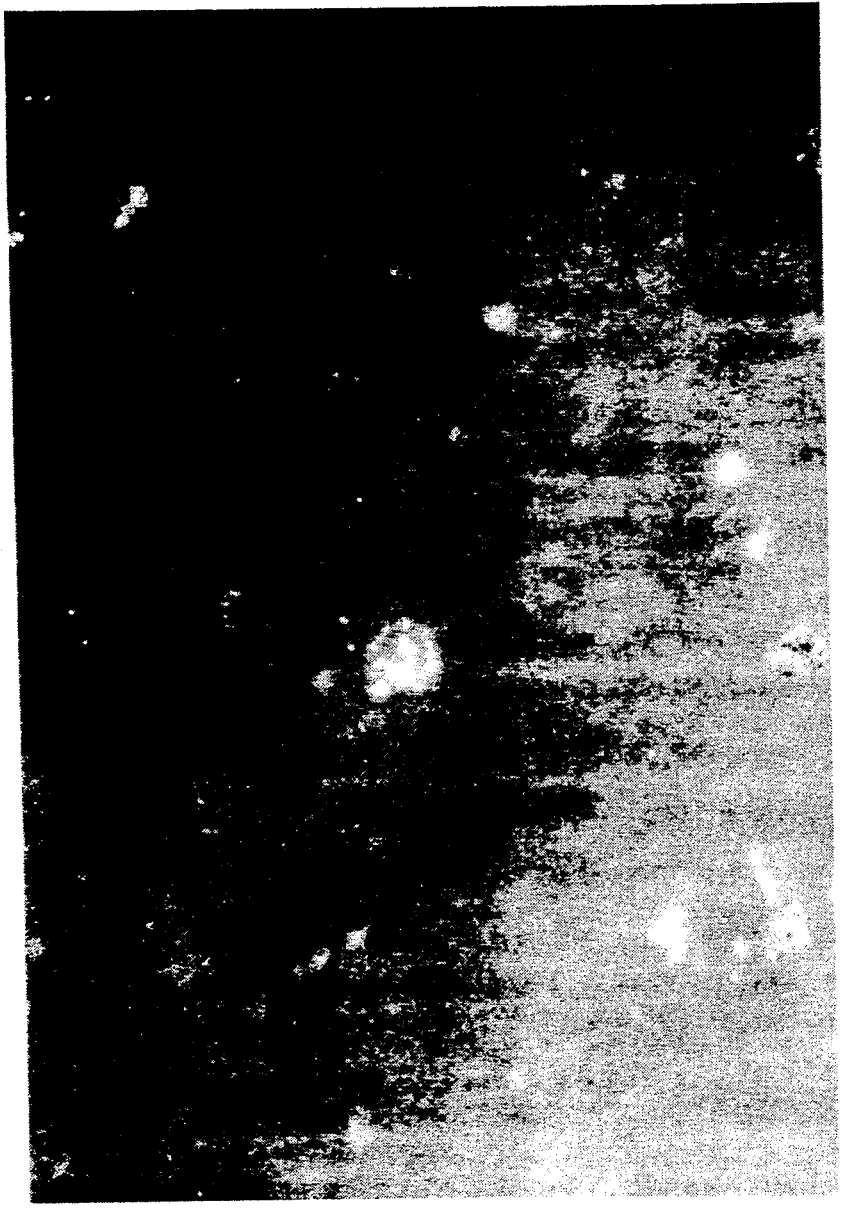

ELISA results for 34 culture supernatants collected from the first fusion are shown in FIG. 19. ELISA results for 42 culture supernatants collected from the second fusion are shown in FIG. 20. Anti-idiotypic antibody against MAb 7H8 was used for further experiments. P. voelli (17XNL) parasites were treated with anti anti-idiotypic antibodies in sera of mice immunized with anti-idiotypic antibodies to MAb 7H8. (A) fluorescent microscopy and (B) Nomarski differential-interference-contrast microscopy, shown in FIG. 21. Comparison with immunofluorescent patterns produced by MAb 7H8, shown in FIG. 1, reveals that anti anti-idiotypic Abs produced a similar pattern of immunofluorescence as MAb 7H8 when assayed on 17XNL P. voelli.

Having now fully described the invention, it will be apparent to one of ordinary skill that many modifications and changes may be made thereto without departing from the spirit and scope thereof.

What is claimed is:

1. MAb 7H8, characterized in that it is produced by the continuous hybridoma cell line 7H8, said cell line having Accession Number ATCC HB 9287.

2. Hybridoma cell line 7H8, having Accession Number ATCC HB 9287.

3. A monoclonal antibody having specific binding affinity for a pan-malarial antigen, said monoclonal antibody characterized in that it has the specificity of MAb 7H8 (ATCC HB9287), or fragments thereof.

4. A monoclonal antibody which specifically binds to the Pf93 antigen, said monoclonal antibody characterized in that it has the specificity of MAb 7H8 (ATCC HB9287), or fragments thereof.

* * * * *

UNITED STATES PATENT AND TRADEMARK OFFICE
CERTIFICATE OF CORRECTION

PATENT NO. : 5,001,225

DATED : March 19, 1991

INVENTOR(S) : Taylor, D. W.

It is certified that error appears in the above-identified patent and that said Letters Patent is hereby corrected as shown below:

In column 1, after line 5, please insert the following:

--This invention was made with government support under Grant No. AI 19874 awarded by the National Institutes of Health. The government has certain rights in the invention.--

Signed and Sealed this

Twenty-sixth Day of April, 1994

Attest:

BRUCE LEHMAN

*Attesting Officer*  *Commissioner of Patents and Trademarks*